United States Patent [19]

Sibley et al.

[11] Patent Number: 5,610,282

[45] Date of Patent: Mar. 11, 1997

[54] CDNA ENCODING A RAT $D_1$ DOPAMINE RECEPTOR LINKED TO ADENYLYL CYCLASE ACTIVATION AND EXPRESSION OF THE RECEPTOR PROTEIN IN PLASMID-TRANSFECTED CELL LINES

[75] Inventors: David R. Sibley, Rockville; Frederick J. Monsma, Baltimore; Lawrence C. Mahan; Loris D. McVittie, both of Bethesda, all of Md.

[73] Assignee: The United States of America as represented by the Department of Health and Human Services, Washington, D.C.

[21] Appl. No.: 444,734

[22] Filed: May 19, 1995

Related U.S. Application Data

[63] Continuation of Ser. No. 29,917, Mar. 11, 1993, abandoned, which is a continuation of Ser. No. 548,714, Jul. 6, 1990, abandoned.

[51] Int. Cl.⁶ .................... C07K 14/705; C07K 14/47; C12N 15/86; C07H 21/04
[52] U.S. Cl. .................... 530/395; 530/350; 536/23.5; 536/24.31; 435/252.3; 435/320.1; 435/69.1; 935/9; 935/27; 935/32; 935/71; 935/73
[58] Field of Search .................... 536/23.5, 24.31; 435/69.1, 320.1, 240.2, 252.3; 530/350, 395

[56] References Cited

U.S. PATENT DOCUMENTS 4,675,285  6/1987  Clark et al. .................... 435/6
5,389,543  2/1995  Bunzow et al. .................... 435/252.3

OTHER PUBLICATIONS

"Laboratory techniques in Biochemistry and Molecular Biology", Elsevier, 1984, pp. 67–253.
Sunahara et al, "Cloning of the gene for a human dopamine $D_5$ receptor with higher affinity for doamine than $D_1$", Letters to Nature, Apr. 18, 1991, vol. 350, pp. 614–619.
Tiberi et al, "Cloning, molecular Characterization, and chromosomal assignment of a gene encoding a second $D_1$ dopamine receptor subtype: Differential expression pattern in rat brain compared with the $D_{1A}$ receptor", Neurobiology, Sep. 1991, vol. 88, pp. 7491–7495.
Dearry et al, "Molecular cloning and expression of the gene for a human $D_1$ dopamine receptor", Nature, Sep. 6, 1990, vol. 347, pp. 72–75.
Zhou et al, "Cloning and expression of human and rat $D_1$ dopamine receptors", Nature, Sep. 6, 1990, vol. 347 pp. 76–79.
Minowa et al, "Characterization of the 5' flanking region of the human $D_{1A}$ dopamine receptor gene", Biochemistry, Apr. 1992, pp. 3045–3049.

(List continued on next page.)

Primary Examiner—Robert A. Wax
Assistant Examiner—William W. Moore
Attorney, Agent, or Firm—Knobbe Martens Olson & Bear

[57] ABSTRACT

The present invention relates to the molecular cloning and expression of the $D_1$ dopamine receptor protein that is linked to the activation of adenylyl cyclase activity. By constructing cell lines that express the $D_1$ receptor, the affinities and efficacies of agonist and antagonist drugs with the receptor can be assessed.

The present invention further relates to a recombinant DNA construct that includes a vector and a DNA fragment encoding the $D_1$ receptor. The present invention also relates to a host cell transformed with a recombinant DNA construct, so that the DNA fragment is expressed and the $D_1$ receptor is produced. Suitable expression systems include eukaryotic and procaryotic cells, especially mammalian cells such as rat or human.

The present invention further relates to the antibody to the $D_1$ receptor protein. For diagnostic purposes, antibodies to this receptor can be prepared by producing all or a portion of the receptor protein and injecting these into various types of mammals. Using the resulting antibodies, expression of the $D_1$ receptor cDNA in cells can be measured.

9 Claims, 3 Drawing Sheets

OTHER PUBLICATIONS

Sunahara et al, "Human dopamine $D_1$ receptor encoded by an intronless gene on chromosome 5", *Nature*, Sep. 6, 1990, vol. 347, pp. 80–83.

Day, R. A. 1983. How to Write and Publish a Scientific Paper; iSi Press, Philadelphia, PA., pp. 15–19.

Monsma et al. 1990 Proc. Natl. Acad. Sci. 87(17):6723–6727.

Abstract, DIALOG File 155 accession No. 91359232 of Singrich et al. 1991. J. Recept. Res. 11(1–4):521–534.

Bunzow et al. 1988 Nature, 336: 783–787.

Sengrich et al. 1988. Biochemistry 27:3907–3912.

Sofer et al. Nov./Dec. 1983. Bio/Techniques pp. 198–203.

Semi et al. 1988. Science 241: 585–589.

Young et al. 1983. Proc. Natl. Acad. Sci. 80:1194–1198.

Dearry et al. Sep. 1990. Nature 347: 72–75.

Zhou et al. Sep. 1990, Nature 347:76–79.

Sunahara et al. Sep. 1990. Nature 347:80–83.

Niznik et al. 1988. Biochemistry 27:7594–7599.

Alberts et al. 1983. *Molecular Biology of the Cell,* Garland Publishing Inc., N.Y., NY. pp. 185–196.

Campbell, A. M. 1985. *Monoclonal Antibody Technology* (eds.) Burdon, R. H. and Van Korippberg, P. H., Elsevier, NY. pp. 61–101, 120–215 and 243–255.

Searing et al. 1989. The EMBO Journal. 8(12):3667–3676.

Andersen et al. Jun. 1990. Trends Pharmacol. Sci. 11(6):231–236 (Abstract Only).

Matsudaira, p. 1987. J. Biol. Chem. 262(21):10035–10038.

Gingrich et al., Abstract, DIALOG File 155 accession No.: 91359232, J. Recept. Res. 1991, 11(1–4): 521–534.

Pongor, S. 1987. Methods in Enzymology, 154:450–473.

Aebersold et al. 1986. J. Biol. Chem. 261(9):4229–4238.

SEQUENCE LISTING ( 1 ) GENERAL INFORMATION:

( i i i ) NUMBER OF SEQUENCES: 13

( 2 ) INFORMATION FOR SEQ ID NO:1:

(i) SEQUENCE CHARACTERISTICS:
    (A) LENGTH: 3025 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vii) IMMEDIATE SOURCE:
    (B) CLONE: pB73D1

(ix) FEATURE:
    (A) NAME/KEY: CDS
    (B) LOCATION: 293..1756

(xi) SEQUENCE DESCRIPTION: SEQ ID NO:1:

```
CCGAAGATTC AGAGCCGCAC ATCCCCCTTA TCGATGACAC TGATGCTGAA GATGACGCTC      60

CTACTAAACG CAACTCCAGC CCTCCGCCCT CTCCTAACAA AATAACAAT GCCGTTGACA     120

GCGGGATCCA CCTTACAATA GAAATGAACA AGTCTGCTAC CTCTTCGTCC CCAGGGAGCC    180

CACTGCATAG TTTGGAAACA TCACTCTGAT TGTAAGCTGA ACGTTAACAC ACTAGCCGCA    240

CTGTAAAGAA ACAAATTGAA ACTGAGTCTT TTCACACATT GTGACGGACA AG ATG        295
                                                          Met
                                                            1

GCG TTC TTG TCT CCG GAC TTC AAC AGA AGA CAC ACT TGT ACG AAT GTA      343
Ala Phe Leu Ser Pro Asp Phe Asn Arg Arg His Thr Cys Thr Asn Val
              5                  10                  15

GAT TTA TTT GTC TGG CTA AGC CTG GTC AAG AAC TTG AGG GGC AAG TCC      391
Asp Leu Phe Val Trp Leu Ser Leu Val Lys Asn Leu Arg Gly Lys Ser
         20                  25                  30

CCG GAA GTG TGT TCC TTC TGG AAG ATG GCT CCT AAC ACT TCT ACC ATG      439
Pro Glu Val Cys Ser Phe Trp Lys Met Ala Pro Asn Thr Ser Thr Met
     35                  40                  45

GAT GAG GCC GGG CTG CCA GCG GAG AGG GAT TTC TCC TTT CGC ATC CTC      487
Asp Glu Ala Gly Leu Pro Ala Glu Arg Asp Phe Ser Phe Arg Ile Leu
 50                  55                  60                  65

ACG GCC TGT TTC CTG TCA CTG CTC ATC CTG TCC ACT CTC CTG GGC AAT      535
Thr Ala Cys Phe Leu Ser Leu Leu Ile Leu Ser Thr Leu Leu Gly Asn
                 70                  75                  80

ACC CTT GTC TGT GCG GCC GTC ATC CGG TTT CGA CAC CTG AGG TCC AAG      583
Thr Leu Val Cys Ala Ala Val Ile Arg Phe Arg His Leu Arg Ser Lys
             85                  90                  95

GTG ACC AAC TTC TTT GTC ATC TCT TTA GCT GTG TCA GAT CTC TTG GTG      631
Val Thr Asn Phe Phe Val Ile Ser Leu Ala Val Ser Asp Leu Leu Val
         100                 105                 110

GCT GTC CTG GTC ATG CCC TGG AAA GCT GTG GCC GAG ATT GCT GGC TTT      679
Ala Val Leu Val Met Pro Trp Lys Ala Val Ala Glu Ile Ala Gly Phe
     115                 120                 125

TGG CCT TTG GGT CCC TTT TGT AAC ATC TGG GTA GCC TTT GAC ATC ATG      727
Trp Pro Leu Gly Pro Phe Cys Asn Ile Trp Val Ala Phe Asp Ile Met
130                 135                 140                 145

TGC TCT ACG GCG TCC ATT CTG AAC CTC TGC GTG ATC AGC GTG GAC AGG      775
Cys Ser Thr Ala Ser Ile Leu Asn Leu Cys Val Ile Ser Val Asp Arg
                150                 155                 160

TAC TGG GCT ATC TCC AGC CCT TTC CAG TAT GAG AGG AAG ATG ACC CCC      823
Tyr Trp Ala Ile Ser Ser Pro Phe Gln Tyr Glu Arg Lys Met Thr Pro
            165                 170                 175

AAA GCA GCC TTC ATC CTG ATT AGC GTA GCA TGG ACT CTG TCT GTC CTT      871
Lys Ala Ala Phe Ile Leu Ile Ser Val Ala Trp Thr Leu Ser Val Leu
        180                 185                 190
```

| | | | | | | | | | | | | | | | | |
|---|---|---|---|---|---|---|---|---|---|---|---|---|---|---|---|---|
| ATA | TCC | TTC | ATC | CCA | GTA | CAG | CTA | AGC | TGG | CAC | AAG | GCA | AAG | CCC | ACA | 919 |
| Ile | Ser | Phe | Ile | Pro | Val | Gln | Leu | Ser | Trp | His | Lys | Ala | Lys | Pro | Thr | |
| | 195 | | | | 200 | | | | | 205 | | | | | | |
| TGG | CCC | TTG | GAT | GGC | AAT | TTT | ACC | TCC | CTG | GAG | GAC | ACC | GAG | GAT | GAC | 967 |
| Trp | Pro | Leu | Asp | Gly | Asn | Phe | Thr | Ser | Leu | Glu | Asp | Thr | Glu | Asp | Asp | |
| 210 | | | | | 215 | | | | | 220 | | | | | 225 | |
| AAC | TGT | GAC | ACA | AGG | TTG | AGC | AGG | ACG | TAT | GCC | ATT | TCA | TCG | TCC | CTC | 1015 |
| Asn | Cys | Asp | Thr | Arg | Leu | Ser | Arg | Thr | Tyr | Ala | Ile | Ser | Ser | Ser | Leu | |
| | | | | 230 | | | | | 235 | | | | | 240 | | |
| ATC | AGC | TTT | TAC | ATC | CCC | GTA | GCC | ATT | ATG | ATC | GTC | ACC | TAC | ACC | AGT | 1063 |
| Ile | Ser | Phe | Tyr | Ile | Pro | Val | Ala | Ile | Met | Ile | Val | Thr | Tyr | Thr | Ser | |
| | | | 245 | | | | | 250 | | | | | 255 | | | |
| ATC | TAC | AGG | ATT | GCC | CAG | AAG | CAA | ATC | CGG | CGC | ATC | TCA | GCC | TTG | GAG | 1111 |
| Ile | Tyr | Arg | Ile | Ala | Gln | Lys | Gln | Ile | Arg | Arg | Ile | Ser | Ala | Leu | Glu | |
| | | 260 | | | | 265 | | | | | 270 | | | | | |
| AGG | GCA | GCA | GTC | CAT | GCC | AAG | AAT | TGC | CAG | ACC | ACC | GCA | GGT | AAC | GGG | 1159 |
| Arg | Ala | Ala | Val | His | Ala | Lys | Asn | Cys | Gln | Thr | Thr | Ala | Gly | Asn | Gly | |
| | 275 | | | | | 280 | | | | | 285 | | | | | |
| AAC | CCC | GTC | GAA | TGC | GCC | CAG | TCT | GAA | AGT | TCC | TTT | AAG | ATG | TCC | TTC | 1207 |
| Asn | Pro | Val | Glu | Cys | Ala | Gln | Ser | Glu | Ser | Ser | Phe | Lys | Met | Ser | Phe | |
| 290 | | | | | 295 | | | | | 300 | | | | | 305 | |
| AAG | AGG | GAG | ACG | AAA | GTT | CTA | AAG | ACG | CTG | TCT | GTG | ATC | ATG | GGG | GTG | 1255 |
| Lys | Arg | Glu | Thr | Lys | Val | Leu | Lys | Thr | Leu | Ser | Val | Ile | Met | Gly | Val | |
| | | | | 310 | | | | | 315 | | | | | 320 | | |
| TTT | GTG | TGC | TGC | TGG | CTC | CCT | TTC | TTC | ATC | TCG | AAC | TGT | ATG | GTG | CCC | 1303 |
| Phe | Val | Cys | Cys | Trp | Leu | Pro | Phe | Phe | Ile | Ser | Asn | Cys | Met | Val | Pro | |
| | | | 325 | | | | | 330 | | | | | 335 | | | |
| TTC | TGT | GGC | TCT | GAG | GAG | ACC | CAG | CCA | TTC | TGC | ATC | GAT | TCC | ATC | ACC | 1351 |
| Phe | Cys | Gly | Ser | Glu | Glu | Thr | Gln | Pro | Phe | Cys | Ile | Asp | Ser | Ile | Thr | |
| | | | 340 | | | | | 345 | | | | | 350 | | | |
| TTC | GAT | GTG | TTT | GTG | TGG | TTT | GGG | TGG | GCG | AAT | TCT | TCC | CTG | AAC | CCC | 1399 |
| Phe | Asp | Val | Phe | Val | Trp | Phe | Gly | Trp | Ala | Asn | Ser | Ser | Leu | Asn | Pro | |
| | 355 | | | | | 360 | | | | | 365 | | | | | |
| ATT | ATT | TAT | GCT | TTT | AAT | GCT | GAC | TTC | CAG | AAG | GCG | TTC | TCA | ACC | CTC | 1447 |
| Ile | Ile | Tyr | Ala | Phe | Asn | Ala | Asp | Phe | Gln | Lys | Ala | Phe | Ser | Thr | Leu | |
| 370 | | | | | 375 | | | | | 380 | | | | | 385 | |
| TTA | GGA | TGC | TAC | AGA | CTC | TGC | CCT | ACT | ACG | AAT | AAT | GCC | ATA | GAG | ACG | 1495 |
| Leu | Gly | Cys | Tyr | Arg | Leu | Cys | Pro | Thr | Thr | Asn | Asn | Ala | Ile | Glu | Thr | |
| | | | | 390 | | | | | 395 | | | | | 400 | | |
| GTG | AGC | ATT | AAC | AAC | AAT | GGG | GCT | GTG | GTG | TTT | TCC | AGC | CAC | CAT | GAG | 1543 |
| Val | Ser | Ile | Asn | Asn | Asn | Gly | Ala | Val | Val | Phe | Ser | Ser | His | His | Glu | |
| | | | 405 | | | | | 410 | | | | | 415 | | | |
| CCC | CGA | GGC | TCC | ATC | TCC | AAG | GAC | TGT | AAT | CTG | GTT | TAC | CTG | ATC | CCT | 1591 |
| Pro | Arg | Gly | Ser | Ile | Ser | Lys | Asp | Cys | Asn | Leu | Val | Tyr | Leu | Ile | Pro | |
| | | 420 | | | | 425 | | | | | 430 | | | | | |
| CAT | GCC | GTG | GGC | TCC | TCT | GAG | GAC | CTG | AAG | AAG | GAA | GAG | GCT | GGT | GGA | 1639 |
| His | Ala | Val | Gly | Ser | Ser | Glu | Asp | Leu | Lys | Lys | Glu | Glu | Ala | Gly | Gly | |
| | 435 | | | | | 440 | | | | | 445 | | | | | |
| ATA | GCT | AAG | CCA | CTG | GAG | AAG | CTG | TCC | CCA | GCC | TTA | TCG | GTC | ATA | TTG | 1687 |
| Ile | Ala | Lys | Pro | Leu | Glu | Lys | Leu | Ser | Pro | Ala | Leu | Ser | Val | Ile | Leu | |
| 450 | | | | | 455 | | | | | 460 | | | | | 465 | |
| GAC | TAT | GAC | ACC | GAT | GTC | TCT | CTA | GAA | AAG | ATC | CAA | CCT | GTC | ACA | CAC | 1735 |
| Asp | Tyr | Asp | Thr | Asp | Val | Ser | Leu | Glu | Lys | Ile | Gln | Pro | Val | Thr | His | |
| | | | | 470 | | | | | 475 | | | | | 480 | | |
| AGT | GGA | CAG | CAT | TCC | ACT | TGAATATTGG | GTCCTCATCT | CTGAGGCCAC | | | | | | | | 1783 |
| Ser | Gly | Gln | His | Ser | Thr | | | | | | | | | | | |
| | | | 485 | | | | | | | | | | | | | |

| | | | |
|---|---|---|---|
| GAGTTCCCTT | GGGCTTGCTG | TTAAGGAATT | AACAGGAGAT CCCTCTGCTG CTTTTGGACA | 1843 |
| ATTACGAAGC | TTCTCAAACT | CACTGATTCC | AGTGTATTCT CTAGCTTCAA GGGAAATGAC | 1903 |

```
TTCGGCTCTG  AAATCAGTTT  GGGAGTATTA  TCTTAGGACA  TTATAAAACA  ACAACAAACA   1963

AACAAACAAA  CAAACAAATA  GGCCAAGAGT  CAACTGTAAA  CAGCTTCACT  TAAAAATCGA   2023

ACTTTCCAGA  AAGGAAGGGT  AGGAGTTGAG  TTTGCTGTCC  AAACAGGTGC  TAAAACTGTC   2083

CGAGCAGTTT  TCAGATTGGA  AAGGTAGGTG  CATGCCTTTG  TTAATTAACT  TCTCCAATAA   2143

TAATTGAGCC  TTACAGCAGG  AGTGGGATTC  CTTTTCTCA   GAATTGACAG  ATGCATTGTT   2203

GATGACGGTT  TTATTTATTT  ATTTATTGTA  CTATATGAAT  ATTTTAAATT  TATCATAGTG   2263

AATCTATATT  TAACATATTT  AACAGAGCAA  ACCAATGTGT  TATCTGAGAC  TGACCTCTCC   2323

ATTTGTACTA  GCACTTTATG  AGCCAATGAA  ACATACGCGT  AGACTCTGAG  ATTCTGAATT   2383

GTGAGTTACT  TCTGGGAACA  CAGCAAAGAC  TGATGTGGTG  GCTCCTTAAC  TCGACAAGGA   2443

CACAAAGAAA  CGCAAGAGGA  GAAGTGACTA  ATGCCACCAA  TGCTCCCCCT  AAAAAGATTT   2503

TGAAAAGATT  AGTTTTTTTT  TTTTTTAAA   AGAAGCTACT  ATTGTGTTCT  GAATGTTTTA   2563

AATGGCAGAG  CTTTCCCCG   GGGCGAATTC  CGGCCGGTAA  TGCAAGCTCC  TGGGGCTTGG   2623

GCTGTGGTGT  TTTGTTCTGT  GTGTGGCCCA  GGGGCAGTGT  GACCCAACTA  CTCCCCTTTG   2683

CCCAGCCAGC  AGCCATTGTT  CTTTCATAGT  TGTTTAATTT  ACATCATAAT  ATGTTGAATC   2743

TCAGGTAAAT  GAGGTCTGTA  TTTGGTAAGT  TTTATCTTGA  CAGAAAGGCC  AGCCTGGTCT   2803

TCCCGACCCT  TCCTGTCCAC  ATTAAAACTG  AATTAAGTGT  CCATGAGTTT  CTGGGCCAGG   2863

TGTGTGGCTT  AGCATTGACC  TTCATGACCT  TACATAGCTC  TTTAGAGAAG  CCATAACAAT   2923

TAGATTGCAA  TACTAATCAG  AATGCCCTCT  GCCCAAAGAG  ATGACGCATG  CTCAGCTCAG   2983

CCCACAGTAC  CTTGCTCACC  TGGGCCACTC  TCTGCGGGAA  TT                       3025
```

( 2 ) INFORMATION FOR SEQ ID NO:2:

( i ) SEQUENCE CHARACTERISTICS:
  ( A ) LENGTH: 487 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Ala Phe Leu Ser Pro Asp Phe Asn Arg Arg His Thr Cys Thr Asn
 1               5                  10                  15

Val Asp Leu Phe Val Trp Leu Ser Leu Val Lys Asn Leu Arg Gly Lys
            20                  25                  30

Ser Pro Glu Val Cys Ser Phe Trp Lys Met Ala Pro Asn Thr Ser Thr
        35                  40                  45

Met Asp Glu Ala Gly Leu Pro Ala Glu Arg Asp Phe Ser Phe Arg Ile
    50                  55                  60

Leu Thr Ala Cys Phe Leu Ser Leu Leu Ile Leu Ser Thr Leu Leu Gly
65                  70                  75                  80

Asn Thr Leu Val Cys Ala Ala Val Ile Arg Phe Arg His Leu Arg Ser
                85                  90                  95

Lys Val Thr Asn Phe Phe Val Ile Ser Leu Ala Val Ser Asp Leu Leu
            100                 105                 110

Val Ala Val Leu Val Met Pro Trp Lys Ala Val Ala Glu Ile Ala Gly
        115                 120                 125

Phe Trp Pro Leu Gly Pro Phe Cys Asn Ile Trp Val Ala Phe Asp Ile
    130                 135                 140

Met Cys Ser Thr Ala Ser Ile Leu Asn Leu Cys Val Ile Ser Val Asp
145                 150                 155                 160
```

```
Arg  Tyr  Trp  Ala  Ile  Ser  Ser  Pro  Phe  Gln  Tyr  Glu  Arg  Lys  Met  Thr
               165                      170                     175

Pro  Lys  Ala  Ala  Phe  Ile  Leu  Ile  Ser  Val  Ala  Trp  Thr  Leu  Ser  Val
               180                      185                     190

Leu  Ile  Ser  Phe  Ile  Pro  Val  Gln  Leu  Ser  Trp  His  Lys  Ala  Lys  Pro
          195                      200                     205

Thr  Trp  Pro  Leu  Asp  Gly  Asn  Phe  Thr  Ser  Leu  Glu  Asp  Thr  Glu  Asp
     210                      215                     220

Asp  Asn  Cys  Asp  Thr  Arg  Leu  Ser  Arg  Thr  Tyr  Ala  Ile  Ser  Ser  Ser
225                      230                     235                          240

Leu  Ile  Ser  Phe  Tyr  Ile  Pro  Val  Ala  Ile  Met  Ile  Val  Thr  Tyr  Thr
               245                      250                     255

Ser  Ile  Tyr  Arg  Ile  Ala  Gln  Lys  Gln  Ile  Arg  Arg  Ile  Ser  Ala  Leu
               260                      265                     270

Glu  Arg  Ala  Ala  Val  His  Ala  Lys  Asn  Cys  Gln  Thr  Thr  Ala  Gly  Asn
               275                      280                     285

Gly  Asn  Pro  Val  Glu  Cys  Ala  Gln  Ser  Glu  Ser  Ser  Phe  Lys  Met  Ser
          290                      295                     300

Phe  Lys  Arg  Glu  Thr  Lys  Val  Leu  Lys  Thr  Leu  Ser  Val  Ile  Met  Gly
305                      310                     315                          320

Val  Phe  Val  Cys  Cys  Trp  Leu  Pro  Phe  Phe  Ile  Ser  Asn  Cys  Met  Val
               325                      330                     335

Pro  Phe  Cys  Gly  Ser  Glu  Glu  Thr  Gln  Pro  Phe  Cys  Ile  Asp  Ser  Ile
               340                      345                     350

Thr  Phe  Asp  Val  Phe  Val  Trp  Phe  Gly  Trp  Ala  Asn  Ser  Ser  Leu  Asn
          355                      360                     365

Pro  Ile  Ile  Tyr  Ala  Phe  Asn  Ala  Asp  Phe  Gln  Lys  Ala  Phe  Ser  Thr
     370                      375                     380

Leu  Leu  Gly  Cys  Tyr  Arg  Leu  Cys  Pro  Thr  Thr  Asn  Asn  Ala  Ile  Glu
385                      390                     395                          400

Thr  Val  Ser  Ile  Asn  Asn  Asn  Gly  Ala  Val  Val  Phe  Ser  Ser  His  His
               405                      410                     415

Glu  Pro  Arg  Gly  Ser  Ile  Ser  Lys  Asp  Cys  Asn  Leu  Val  Tyr  Leu  Ile
               420                      425                     430

Pro  His  Ala  Val  Gly  Ser  Ser  Glu  Asp  Leu  Lys  Lys  Glu  Glu  Ala  Gly
          435                      440                     445

Gly  Ile  Ala  Lys  Pro  Leu  Glu  Lys  Leu  Ser  Pro  Ala  Leu  Ser  Val  Ile
          450                      455                     460

Leu  Asp  Tyr  Asp  Thr  Asp  Val  Ser  Leu  Glu  Lys  Ile  Gln  Pro  Val  Thr
465                      470                     475                          480

His  Ser  Gly  Gln  His  Ser  Thr
                    485
```

( 2 ) INFORMATION FOR SEQ ID NO:3:

( i ) SEQUENCE CHARACTERISTICS:
        ( A ) LENGTH: 443 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

| Met | Asp | Pro | Leu | Asn | Leu | Ser | Trp | Tyr | Asp | Asp | Leu | Glu | Arg | Gln |
| 1 | | | | 5 | | | | | 10 | | | | | 15 |

| Asn | Trp | Ser | Arg | Pro | Phe | Asn | Gly | Ser | Glu | Gly | Lys | Ala | Asp | Arg | Pro |
| | | | 20 | | | | | 25 | | | | | 30 | | |

| His | Tyr | Asn | Tyr | Tyr | Ala | Met | Leu | Leu | Thr | Leu | Leu | Ile | Phe | Ile | Ile |
| | | 35 | | | | | 40 | | | | | | 45 | | |

| Val | Phe | Asn | Val | Leu | Val | Cys | Met | Ala | Val | Ser | Arg | Glu | Lys | Ala | Leu |
| | 50 | | | | | 55 | | | | | 60 | | | | |

| Gln | Thr | Thr | Thr | Asn | Tyr | Leu | Ile | Val | Ser | Leu | Ala | Val | Ala | Asp | Leu |
| 65 | | | | | 70 | | | | | 75 | | | | | 80 |

| Leu | Val | Ala | Ile | Leu | Val | Met | Pro | Trp | Val | Val | Tyr | Leu | Glu | Val | Val |
| | | | | 85 | | | | | 90 | | | | | 95 | |

| Gly | Glu | Trp | Lys | Phe | Ser | Arg | Ile | His | Cys | Asp | Ile | Phe | Val | Thr | Leu |
| | | | 100 | | | | | 105 | | | | | 110 | | |

| Asp | Val | Met | Met | Cys | Thr | Ala | Ser | Ile | Leu | Asn | Leu | Cys | Ala | Ile | Ser |
| | | 115 | | | | | 120 | | | | | 125 | | | |

| Ile | Asp | Arg | Tyr | Thr | Ala | Val | Ala | Met | Pro | Met | Leu | Tyr | Asn | Thr | Arg |
| | 130 | | | | | 135 | | | | | 140 | | | | |

| Tyr | Ser | Ser | Lys | Arg | Arg | Val | Thr | Val | Met | Ile | Ala | Ile | Val | Trp | Val |
| 145 | | | | | 150 | | | | | 155 | | | | | 160 |

| Leu | Ser | Phe | Thr | Ile | Ser | Cys | Pro | Leu | Leu | Phe | Gly | Leu | Asn | Asn | Thr |
| | | | | 165 | | | | | 170 | | | | | 175 | |

| Asp | Gln | Asn | Glu | Cys | Ile | Ile | Ala | Asn | Pro | Ala | Phe | Val | Val | Tyr | Ser |
| | | | 180 | | | | | 185 | | | | | 190 | | |

| Ser | Ile | Val | Ser | Phe | Tyr | Val | Pro | Phe | Ile | Val | Thr | Leu | Leu | Val | Tyr |
| | | 195 | | | | | 200 | | | | | 205 | | | |

| Ile | Lys | Ile | Tyr | Ile | Val | Leu | Arg | Lys | Arg | Arg | Lys | Arg | Val | Asn | Thr |
| | 210 | | | | | 215 | | | | | 220 | | | | |

| Lys | Arg | Ser | Ser | Arg | Ala | Phe | Arg | Ala | Asn | Leu | Lys | Thr | Pro | Leu | Lys |
| 225 | | | | | 230 | | | | | 235 | | | | | 240 |

| Gly | Asn | Cys | Thr | His | Pro | Glu | Asp | Met | Lys | Leu | Cys | Thr | Val | Ile | Met |
| | | | | 245 | | | | | 250 | | | | | 255 | |

| Lys | Ser | Asn | Gly | Ser | Phe | Pro | Val | Val | Asn | Arg | Arg | Arg | Met | Asp | Ala |
| | | | 260 | | | | | 265 | | | | | 270 | | |

| Ala | Arg | Arg | Ala | Gln | Glu | Leu | Met | Glu | Met | Leu | Ser | Ser | Thr | Ser | Pro |
| | | 275 | | | | | 280 | | | | | 285 | | | |

| Pro | Glu | Arg | Thr | Arg | Tyr | Ser | Pro | Ile | Pro | Pro | Ser | His | His | Gln | Leu |
| | 290 | | | | | 295 | | | | | 300 | | | | |

| Thr | Leu | Pro | Asp | Pro | Ser | His | His | Gly | Leu | His | Ser | Asn | Pro | Asp | Ser |
| 305 | | | | | 310 | | | | | 315 | | | | | 320 |

| Pro | Ala | Lys | Pro | Glu | Lys | Asn | Gly | His | Ala | Lys | Ile | Val | Asn | Pro | Arg |
| | | | | 325 | | | | | 330 | | | | | 335 | |

| Ile | Ala | Lys | Phe | Phe | Glu | Ile | Gln | Thr | Met | Pro | Asn | Gly | Lys | Thr | Arg |
| | | | 340 | | | | | 345 | | | | | 350 | | |

| Thr | Ser | Leu | Lys | Thr | Met | Ser | Arg | Arg | Lys | Leu | Ser | Gln | Gln | Lys | Glu |
| | | | 355 | | | | | 360 | | | | | 365 | | |

| Lys | Lys | Ala | Thr | Gln | Met | Leu | Ala | Ile | Val | Leu | Gly | Val | Phe | Ile | Ile |
| | | 370 | | | | | 375 | | | | | 380 | | | |

| Cys | Trp | Leu | Pro | Phe | Phe | Ile | Thr | His | Ile | Leu | Asn | Ile | His | Cys | Asp |
| 385 | | | | | 390 | | | | | 395 | | | | | 400 |

| Cys | Asn | Ile | Pro | Pro | Val | Leu | Tyr | Ser | Ala | Phe | Thr | Trp | Leu | Gly | Tyr |
| | | | | 405 | | | | | 410 | | | | | 415 | |

```
          Val  Asn  Ser  Ala  Val  Asn  Pro  Ile  Ile  Tyr  Thr  Thr  Phe  Asn  Ile  Glu
                         420                 425                      430

Phe  Arg  Lys  Ala  Phe  Met  Lys  Ile  Leu  His  Cys
                         435                 440
```

( 2 ) INFORMATION FOR SEQ ID NO:4:

( i ) SEQUENCE CHARACTERISTICS:
       ( A ) LENGTH: 477 amino acids
       ( B ) TYPE: amino acid
       ( C ) STRANDEDNESS: single
       ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

```
          Met  Gly  Ala  Gly  Val  Leu  Val  Leu  Gly  Ala  Ser  Glu  Pro  Gly  Asn  Leu
          1              5                        10                       15

Ser  Ser  Ala  Ala  Pro  Leu  Pro  Asp  Gly  Ala  Ala  Thr  Ala  Ala  Arg  Leu
                         20                       25                       30

Leu  Val  Pro  Ala  Ser  Pro  Pro  Ala  Ser  Leu  Leu  Pro  Pro  Ala  Ser  Glu
                    35                            40                       45

Ser  Pro  Glu  Pro  Leu  Ser  Gln  Gln  Trp  Thr  Ala  Gly  Met  Gly  Leu  Leu
                    50                       55                  60

Met  Ala  Leu  Ile  Glu  Leu  Leu  Ile  Val  Ala  Gly  Asn  Val  Leu  Val  Ile
          65                       70                       75                            80

Val  Ala  Ile  Ala  Lys  Thr  Pro  Arg  Leu  Gln  Thr  Leu  Thr  Asn  Leu  Phe
                              85                       90                            95

Ile  Met  Ser  Leu  Ala  Ser  Ala  Asp  Leu  Val  Met  Gly  Leu  Leu  Val  Val
                         100                      105                      110

Pro  Phe  Gly  Ala  Thr  Ile  Val  Val  Trp  Gly  Arg  Trp  Glu  Tyr  Gly  Ser
                         115                      120                      125

Phe  Phe  Cys  Glu  Leu  Trp  Thr  Ser  Val  Asp  Val  Leu  Cys  Val  Thr  Ala
                    130                      135                      140

Ser  Ile  Glu  Thr  Leu  Cys  Val  Ile  Ala  Leu  Asp  Arg  Tyr  Leu  Ala  Ile
          145                      150                      155                           160

Thr  Ser  Pro  Phe  Arg  Tyr  Gln  Ser  Leu  Leu  Thr  Arg  Ala  Arg  Ala  Arg
                              165                      170                      175

Gly  Leu  Val  Cys  Thr  Val  Trp  Ala  Ile  Ser  Ala  Leu  Val  Ser  Phe  Leu
                         180                      185                      190

Pro  Ile  Leu  Met  His  Trp  Trp  Arg  Ala  Glu  Ser  Asp  Glu  Ala  Arg  Arg
                    195                      200                      205

Cys  Tyr  Asn  Asp  Pro  Lys  Cys  Cys  Asp  Phe  Val  Thr  Asn  Arg  Ala  Tyr
                    210                      215                      220

Ala  Ile  Ala  Ser  Ser  Val  Val  Ser  Phe  Tyr  Val  Pro  Leu  Cys  Ile  Met
          225                      230                      235                           240

Ala  Phe  Val  Tyr  Leu  Arg  Val  Phe  Arg  Glu  Ala  Gln  Lys  Gln  Val  Lys
                              245                      250                      255

Lys  Ile  Asp  Ser  Cys  Glu  Arg  Arg  Phe  Leu  Gly  Gly  Pro  Ala  Arg  Pro
                         260                      265                      270

Pro  Ser  Pro  Ser  Pro  Ser  Pro  Val  Pro  Ala  Pro  Ala  Pro  Pro  Pro  Gly
                         275                      280                      285
```

```
Pro  Pro  Arg  Pro  Ala  Ala  Ala  Ala  Thr  Ala  Pro  Leu  Ala  Asn  Gly
     290                 295                      300

Arg  Ala  Gly  Lys  Arg  Arg  Pro  Ser  Arg  Leu  Val  Ala  Leu  Arg  Glu  Gln
305                      310                 315                           320

Lys  Ala  Leu  Lys  Thr  Leu  Gly  Ile  Ile  Met  Gly  Val  Phe  Thr  Leu  Cys
                    325                      330                      335

Trp  Leu  Pro  Phe  Phe  Leu  Ala  Asn  Val  Val  Lys  Ala  Phe  His  Arg  Glu
               340                 345                           350

Leu  Val  Pro  Asp  Arg  Leu  Phe  Val  Phe  Phe  Asn  Trp  Leu  Gly  Tyr  Ala
               355                 360                      365

Asn  Ser  Ala  Phe  Asn  Pro  Ile  Ile  Tyr  Cys  Arg  Ser  Pro  Asp  Phe  Arg
     370                      375                      380

Lys  Ala  Phe  Gln  Gly  Leu  Leu  Cys  Cys  Ala  Arg  Arg  Ala  Ala  Arg  Arg
385                      390                      395                      400

Arg  His  Ala  Thr  His  Gly  Asp  Arg  Pro  Arg  Ala  Ser  Gly  Cys  Leu  Ala
                    405                      410                      415

Arg  Pro  Gly  Pro  Pro  Pro  Ser  Pro  Gly  Ala  Ala  Ser  Asp  Asp  Asp  Asp
               420                      425                 430

Asp  Asp  Val  Val  Gly  Ala  Thr  Pro  Pro  Ala  Arg  Leu  Leu  Glu  Pro  Trp
          435                      440                 445

Ala  Gly  Cys  Asn  Gly  Gly  Ala  Ala  Ala  Asp  Ser  Asp  Ser  Ser  Leu  Asp
     450                      455                 460

Glu  Pro  Cys  Arg  Pro  Gly  Phe  Ala  Ser  Glu  Ser  Lys  Val
465                      470                 475
```

( 2 ) INFORMATION FOR SEQ ID NO:5:

( i ) SEQUENCE CHARACTERISTICS:
        ( A ) LENGTH: 413 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

```
Met  Gly  Gln  Pro  Gly  Asn  Gly  Ser  Ala  Phe  Leu  Leu  Ala  Pro  Asn  Arg
1                   5                    10                      15

Ser  His  Ala  Pro  Asp  His  Asp  Val  Thr  Gln  Gln  Arg  Asp  Glu  Val  Trp
               20                 25                      30

Val  Val  Gly  Met  Gly  Ile  Val  Met  Ser  Leu  Ile  Val  Leu  Ala  Ile  Val
          35                   40                 45

Phe  Gly  Asn  Val  Leu  Val  Ile  Thr  Ala  Ile  Ala  Lys  Phe  Glu  Arg  Leu
     50                      55                      60

Gln  Thr  Val  Thr  Asn  Tyr  Phe  Ile  Thr  Ser  Leu  Ala  Cys  Ala  Asp  Leu
65                       70                 75                           80

Val  Met  Gly  Leu  Ala  Val  Val  Pro  Phe  Gly  Ala  Ala  His  Ile  Leu  Met
               85                      90                      95

Lys  Met  Trp  Thr  Phe  Gly  Asn  Phe  Trp  Cys  Glu  Phe  Trp  Thr  Ser  Ile
               100                     105                     110

Asp  Val  Leu  Cys  Val  Thr  Ala  Ser  Ile  Glu  Thr  Leu  Cys  Val  Ile  Ala
          115                     120                     125

Val  Asp  Arg  Tyr  Phe  Ala  Ile  Thr  Ser  Pro  Phe  Lys  Tyr  Gln  Ser  Leu
```

|     | 130 |     |     |     | 135 |     |     |     |     | 140 |     |     |     |     |
|-----|-----|-----|-----|-----|-----|-----|-----|-----|-----|-----|-----|-----|-----|-----|
| Leu | Thr | Lys | Asn | Lys | Ala | Arg | Val | Ile | Ile | Leu | Met | Val | Trp | Ile | Val |
| 145 |     |     |     |     | 150 |     |     |     |     | 155 |     |     |     |     | 160 |
| Ser | Gly | Leu | Thr | Ser | Phe | Leu | Pro | Ile | Gln | Met | His | Trp | Tyr | Arg | Ala |
|     |     |     |     | 165 |     |     |     |     | 170 |     |     |     |     | 175 |     |
| Thr | His | Gln | Glu | Ala | Ile | Asn | Cys | Tyr | Ala | Asn | Glu | Thr | Cys | Cys | Asp |
|     |     |     | 180 |     |     |     |     | 185 |     |     |     |     | 190 |     |     |
| Phe | Phe | Thr | Asn | Gln | Ala | Tyr | Ala | Ile | Ala | Ser | Ser | Ile | Val | Ser | Phe |
|     |     | 195 |     |     |     |     | 200 |     |     |     |     | 205 |     |     |     |
| Tyr | Val | Pro | Leu | Val | Ile | Met | Val | Phe | Val | Tyr | Ser | Arg | Val | Phe | Gln |
|     | 210 |     |     |     |     | 215 |     |     |     |     | 220 |     |     |     |     |
| Glu | Ala | Lys | Arg | Gln | Leu | Gln | Lys | Ile | Asp | Lys | Ser | Glu | Gly | Arg | Phe |
| 225 |     |     |     |     | 230 |     |     |     |     | 235 |     |     |     |     | 240 |
| His | Val | Gln | Asn | Leu | Ser | Gln | Val | Glu | Gln | Asp | Gly | Arg | Thr | Gly | His |
|     |     |     |     | 245 |     |     |     |     | 250 |     |     |     |     | 255 |     |
| Gly | Leu | Arg | Arg | Ser | Ser | Lys | Phe | Cys | Leu | Lys | Glu | His | Lys | Ala | Leu |
|     |     |     | 260 |     |     |     |     | 265 |     |     |     |     | 270 |     |     |
| Lys | Thr | Leu | Gly | Ile | Ile | Met | Gly | Thr | Phe | Thr | Leu | Cys | Trp | Leu | Pro |
|     |     | 275 |     |     |     |     | 280 |     |     |     |     | 285 |     |     |     |
| Phe | Phe | Ile | Val | Asn | Ile | Val | His | Val | Ile | Gln | Asp | Asn | Leu | Ile | Arg |
|     | 290 |     |     |     |     | 295 |     |     |     |     | 300 |     |     |     |     |
| Lys | Glu | Val | Tyr | Ile | Leu | Leu | Asn | Trp | Ile | Gly | Tyr | Val | Asn | Ser | Gly |
| 305 |     |     |     |     | 310 |     |     |     |     | 315 |     |     |     |     | 320 |
| Phe | Asn | Pro | Leu | Ile | Tyr | Cys | Arg | Ser | Pro | Asp | Phe | Arg | Ile | Ala | Phe |
|     |     |     |     | 325 |     |     |     |     | 330 |     |     |     |     | 335 |     |
| Gln | Glu | Leu | Leu | Cys | Leu | Arg | Arg | Ser | Ser | Leu | Lys | Ala | Tyr | Gly | Asn |
|     |     |     | 340 |     |     |     |     | 345 |     |     |     |     | 350 |     |     |
| Gly | Tyr | Ser | Ser | Asn | Gly | Asn | Thr | Gly | Glu | Gln | Ser | Gly | Tyr | His | Val |
|     |     | 355 |     |     |     |     | 360 |     |     |     |     | 365 |     |     |     |
| Glu | Gln | Glu | Lys | Glu | Asn | Lys | Leu | Leu | Cys | Glu | Asp | Leu | Pro | Gly | Thr |
|     |     | 370 |     |     |     | 375 |     |     |     |     | 380 |     |     |     |     |
| Glu | Asp | Phe | Val | Gly | His | Gln | Gly | Thr | Val | Pro | Ser | Asp | Asn | Ile | Asp |
| 385 |     |     |     |     | 390 |     |     |     |     | 395 |     |     |     |     | 400 |
| Ser | Gln | Gly | Arg | Asn | Cys | Ser | Thr | Asn | Asp | Ser | Leu | Leu |     |     |     |
|     |     |     |     | 405 |     |     |     |     | 410 |     |     |     |     |     |     |

(2) INFORMATION FOR SEQ ID NO:6:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:6:

| Met | Ala | Pro | Trp | Pro | His | Glu | Asn | Ser | Ser | Leu | Ala | Pro | Trp | Pro | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Pro | Thr | Leu | Ala | Pro | Asn | Thr | Ala | Asn | Thr | Ser | Gly | Leu | Pro | Gly |
|     |     |     | 20  |     |     |     |     | 25  |     |     |     |     | 30  |     |     |
| Val | Pro | Trp | Glu | Ala | Ala | Leu | Ala | Gly | Ala | Leu | Leu | Ala | Leu | Ala | Val |
|     |     |     | 35  |     |     |     |     | 40  |     |     |     |     | 45  |     |     |

| | | | | | | | | | | | | | | | |
|---|---|---|---|---|---|---|---|---|---|---|---|---|---|---|---|
|Leu|Ala|Thr|Val|Gly|Gly|Asn|Leu|Leu|Val|Ile|Val|Ala|Ile|Ala|Trp|
| |50| | | | |55| | | |60| | | | | |
|Thr|Pro|Arg|Leu|Gln|Thr|Met|Thr|Asn|Val|Phe|Val|Thr|Ser|Leu|Ala|
|65| | | | |70| | | |75| | | | | |80|
|Ala|Ala|Asp|Leu|Val|Met|Gly|Leu|Leu|Val|Val|Pro|Pro|Ala|Ala|Thr|
| | | | |85| | | |90| | | | |95| | |
|Leu|Ala|Leu|Thr|Gly|His|Trp|Pro|Leu|Gly|Ala|Thr|Gly|Cys|Glu|Leu|
| | | |100| | | | |105| | | |110| | | |
|Trp|Thr|Ser|Val|Asp|Val|Leu|Cys|Val|Thr|Ala|Ser|Ile|Glu|Thr|Leu|
| | |115| | | | |120| | | | |125| | | |
|Cys|Ala|Leu|Ala|Val|Asp|Arg|Tyr|Leu|Ala|Val|Thr|Asn|Pro|Leu|Arg|
| |130| | | | |135| | | | |140| | | | |
|Tyr|Gly|Ala|Leu|Val|Thr|Lys|Arg|Cys|Ala|Arg|Thr|Ala|Val|Val|Leu|
|145| | | | |150| | | | |155| | | | |160|
|Val|Trp|Val|Val|Ser|Ala|Ala|Val|Ser|Phe|Ala|Pro|Ile|Met|Ser|Gln|
| | | | |165| | | | |170| | | | |175| |
|Trp|Trp|Arg|Val|Gly|Ala|Asp|Ala|Glu|Ala|Gln|Arg|Cys|His|Ser|Asn|
| | | |180| | | | |185| | | | |190| | |
|Pro|Arg|Cys|Cys|Ala|Phe|Ala|Ser|Asn|Met|Pro|Tyr|Val|Leu|Leu|Ser|
| | |195| | | | |200| | | | |205| | | |
|Ser|Ser|Val|Ser|Phe|Tyr|Leu|Pro|Leu|Leu|Val|Met|Leu|Phe|Val|Tyr|
| |210| | | | |215| | | | |220| | | | |
|Ala|Arg|Val|Phe|Val|Val|Ala|Thr|Arg|Gln|Leu|Arg|Leu|Leu|Arg|Gly|
|225| | | | |230| | | | |235| | | | |240|
|Glu|Leu|Gly|Arg|Phe|Pro|Pro|Glu|Glu|Ser|Pro|Pro|Ala|Pro|Ser|Arg|
| | | | |245| | | | |250| | | | |255| |
|Ser|Leu|Ala|Pro|Ala|Pro|Val|Gly|Thr|Cys|Ala|Pro|Pro|Glu|Gly|Val|
| | | |260| | | | |265| | | | |270| | |
|Pro|Ala|Cys|Gly|Arg|Arg|Pro|Ala|Arg|Leu|Leu|Pro|Leu|Arg|Glu|His|
| | |275| | | | |280| | | | |285| | | |
|Arg|Ala|Leu|Cys|Thr|Leu|Gly|Leu|Ile|Met|Gly|Thr|Phe|Thr|Leu|Cys|
| |290| | | | |295| | | | |300| | | | |
|Trp|Leu|Pro|Phe|Phe|Leu|Ala|Asn|Val|Leu|Arg|Ala|Leu|Gly|Gly|Pro|
|305| | | | |310| | | | |315| | | | |320|
|Ser|Leu|Val|Pro|Gly|Pro|Ala|Phe|Leu|Ala|Leu|Asn|Trp|Leu|Gly|Tyr|
| | | | |325| | | | |330| | | | |335| |
|Ala|Asn|Ser|Ala|Phe|Asn|Pro|Leu|Ile|Tyr|Cys|Arg|Ser|Pro|Asp|Phe|
| | | |340| | | | |345| | | | |350| | |
|Arg|Ser|Ala|Phe|Arg|Arg|Leu|Leu|Cys|Arg|Cys|Gly|Arg|Arg|Leu|Pro|
| | |355| | | | |360| | | | |365| | | |
|Pro|Glu|Pro|Cys|Ala|Ala|Ala|Arg|Pro|Ala|Leu|Phe|Pro|Ser|Gly|Val|
| |370| | | | |375| | | | |380| | | | |
|Pro|Ala|Ala|Arg|Ser|Ser|Pro|Ala|Gln|Pro|Arg|Leu|Cys|Gln|Arg|Leu|
|385| | | | |390| | | | |395| | | | |400|
|Asp|Gly| | | | | | | | | | | | | | |

( 2 ) INFORMATION FOR SEQ ID NO:7:

( i ) SEQUENCE CHARACTERISTICS:
        ( A ) LENGTH: 515 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Met Asn Pro Asp Leu Asp Pro Gly His Asn Thr Ser Ala Pro Ala Gln
 1               5                  10                  15

Trp Gly Glu Leu Lys Asp Ala Asn Phe Thr Gly Pro Asn Gln Thr Ser
             20                  25                  30

Ser Asn Ser Thr Leu Pro Gln Leu Asp Val Thr Arg Ala Ile Ser Val
         35                  40                  45

Gly Leu Val Leu Gly Ala Phe Ile Leu Phe Ala Ile Val Gly Asn Ile
     50                  55                  60

Leu Val Ile Leu Ser Val Ala Cys Asn Arg His Leu Arg Thr Pro Thr
 65                  70                  75                  80

Asn Tyr Phe Ile Val Asn Leu Ala Ile Ala Asp Leu Leu Leu Ser Phe
                 85                  90                  95

Thr Val Leu Pro Phe Ser Ala Thr Leu Glu Val Leu Gly Tyr Trp Val
             100                 105                 110

Leu Gly Arg Ile Phe Cys Asp Ile Trp Ala Ala Val Asp Val Leu Cys
             115                 120                 125

Cys Thr Ala Ser Ile Leu Ser Leu Cys Ala Ile Ser Ile Asp Arg Tyr
     130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                 165                 170                 175

Ser Ile Gly Pro Leu Leu Gly Trp Lys Glu Pro Ala Pro Asn Asp Asp
             180                 185                 190

Lys Glu Cys Gly Val Thr Glu Glu Pro Phe Tyr Ala Leu Phe Ser Ser
             195                 200                 205

Leu Gly Ser Phe Tyr Ile Pro Leu Ala Val Ile Leu Val Met Tyr Cys
     210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                 245                 250                 255

Ser Lys Asn Phe His Glu Asp Thr Leu Ser Ser Thr Lys Ala Lys Gly
             260                 265                 270

His Asn Pro Arg Ser Ser Ile Ala Val Lys Leu Phe Lys Phe Ser Arg
             275                 280                 285

Glu Lys Lys Ala Ala Lys Thr Leu Gly Ile Val Val Gly Met Phe Ile
     290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
             325                 330                 335

Gly Tyr Phe Asn Ser Cys Leu Asn Pro Ile Ile Tyr Pro Cys Ser Ser
             340                 345                 350

Lys Glu Phe Lys Arg Ala Phe Met Arg Ile Leu Gly Cys Gln Cys Arg
     355                 360                 365

Ser Gly Arg Arg Arg Arg Arg Arg Arg Arg Leu Gly Ala Cys Ala Tyr
     370                 375                 380
```

|     |     |     |     |     |     |     |     |     |     |     |     |     |     |     |     |
|---|---|---|---|---|---|---|---|---|---|---|---|---|---|---|---|
| Thr | Tyr | Arg | Pro | Trp | Thr | Arg | Gly | Gly | Ser | Leu | Glu | Arg | Ser | Gln | Ser |
| 385 |     |     |     |     | 390 |     |     |     |     | 395 |     |     |     |     | 400 |
| Arg | Lys | Asp | Ser | Leu | Asp | Asp | Ser | Gly | Ser | Cys | Met | Ser | Gly | Ser | Gln |
|     |     |     |     | 405 |     |     |     |     | 410 |     |     |     |     | 415 |     |
| Arg | Thr | Leu | Pro | Ser | Ala | Ser | Pro | Ser | Pro | Gly | Tyr | Leu | Gly | Arg | Gly |
|     |     |     | 420 |     |     |     |     | 425 |     |     |     |     | 430 |     |     |
| Ala | Gln | Pro | Pro | Leu | Glu | Leu | Cys | Ala | Tyr | Gln | Glu | Trp | Lys | Ser | Gly |
|     |     | 435 |     |     |     |     | 440 |     |     |     |     | 445 |     |     |     |
| Ala | Leu | Leu | Ser | Leu | Pro | Glu | Pro | Pro | Gly | Arg | Arg | Gly | Arg | Leu | Asp |
|     | 450 |     |     |     |     | 455 |     |     |     |     | 460 |     |     |     |     |
| Ser | Gly | Pro | Leu | Phe | Thr | Phe | Lys | Leu | Leu | Gly | Glu | Pro | Glu | Ser | Pro |
| 465 |     |     |     |     | 470 |     |     |     |     | 475 |     |     |     |     | 480 |
| Gly | Thr | Glu | Gly | Asp | Ala | Ser | Asn | Gly | Gly | Cys | Asp | Ala | Thr | Thr | Asp |
|     |     |     |     | 485 |     |     |     |     | 490 |     |     |     |     | 495 |     |
| Leu | Ala | Asn | Gly | Gln | Pro | Gly | Phe | Lys | Ser | Asn | Met | Pro | Leu | Ala | Pro |
|     |     |     | 500 |     |     |     |     | 505 |     |     |     |     | 510 |     |     |
| Gly | His | Phe |     |     |     |     |     |     |     |     |     |     |     |     |     |
|     |     | 515 |     |     |     |     |     |     |     |     |     |     |     |     |     |

( 2 ) INFORMATION FOR SEQ ID NO:8:

( i ) SEQUENCE CHARACTERISTICS:
        ( A ) LENGTH: 450 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

|     |     |     |     |     |     |     |     |     |     |     |     |     |     |     |     |
|---|---|---|---|---|---|---|---|---|---|---|---|---|---|---|---|
| Met | Gly | Ser | Leu | Gln | Pro | Asp | Ala | Gly | Asn | Ala | Ser | Trp | Asn | Gly | Thr |
| 1 |     |     |     | 5 |     |     |     |     | 10 |     |     |     |     | 15 |     |
| Glu | Ala | Pro | Gly | Gly | Gly | Ala | Arg | Ala | Thr | Pro | Tyr | Ser | Leu | Gln | Val |
|     |     |     | 20 |     |     |     |     | 25 |     |     |     |     | 30 |     |     |
| Thr | Leu | Thr | Leu | Val | Cys | Leu | Ala | Gly | Leu | Leu | Met | Leu | Leu | Thr | Val |
|     |     | 35 |     |     |     |     | 40 |     |     |     |     | 45 |     |     |     |
| Phe | Gly | Asn | Val | Leu | Tyr | Ile | Ile | Ala | Val | Phe | Thr | Ser | Arg | Ala | Leu |
|     | 50 |     |     |     |     | 55 |     |     |     |     | 60 |     |     |     |     |
| Lys | Ala | Pro | Gln | Asn | Leu | Phe | Leu | Val | Ser | Leu | Ala | Ser | Ala | Asp | Ile |
| 65 |     |     |     |     | 70 |     |     |     |     | 75 |     |     |     |     | 80 |
| Leu | Val | Ala | Thr | Leu | Val | Ile | Pro | Phe | Ser | Leu | Ala | Asn | Glu | Val | Met |
|     |     |     |     | 85 |     |     |     |     | 90 |     |     |     |     | 95 |     |
| Gly | Tyr | Trp | Tyr | Phe | Gly | Lys | Thr | Trp | Cys | Glu | Ile | Tyr | Leu | Ala | Leu |
|     |     |     | 100 |     |     |     |     | 105 |     |     |     |     | 110 |     |     |
| Asp | Val | Leu | Phe | Cys | Thr | Ser | Ser | Ile | Val | His | Leu | Cys | Ala | Ile | Ser |
|     |     | 115 |     |     |     |     | 120 |     |     |     |     | 125 |     |     |     |
| Leu | Asp | Arg | Tyr | Trp | Ser | Ile | Thr | Gln | Ala | Ile | Glu | Tyr | Asn | Leu | Lys |
|     | 130 |     |     |     |     | 135 |     |     |     |     | 140 |     |     |     |     |
| Arg | Thr | Pro | Arg | Arg | Ile | Lys | Ala | Ile | Ile | Thr | Val | Trp | Val | Ile |
| 145 |     |     |     |     | 150 |     |     |     |     | 155 |     |     |     | 160 |
| Ser | Ala | Val | Ile | Ser | Phe | Pro | Pro | Leu | Ile | Ser | Ile | Glu | Lys | Lys | Gly |
|     |     |     |     | 165 |     |     |     |     | 170 |     |     |     |     | 175 |     |
| Gly | Gly | Gly | Gly | Pro | Gln | Pro | Ala | Glu | Pro | Arg | Cys | Glu | Ile | Asn | Asp |

|     |     |     |     |     |     |     |     |     |     |     |     |     |     |     |
|---|---|---|---|---|---|---|---|---|---|---|---|---|---|---|
|     |     |     | 180 |     |     |     |     | 185 |     |     |     |     | 190 |     |
| Gln | Lys | Trp | Tyr | Val | Ile | Ser | Ser | Cys | Ile | Gly | Ser | Phe | Phe | Ala | Pro |
|     |     | 195 |     |     |     |     | 200 |     |     |     | 205 |     |     |     |
| Cys | Leu | Ile | Met | Ile | Leu | Val | Tyr | Val | Arg | Ile | Tyr | Gln | Leu | Ala | Lys |
|     |     | 210 |     |     |     |     | 215 |     |     |     | 220 |     |     |     |
| Arg | Arg | Thr | Arg | Val | Pro | Pro | Ser | Arg | Arg | Gly | Pro | Asp | Ala | Val | Ala |
| 225 |     |     |     |     | 230 |     |     |     |     | 235 |     |     |     |     | 240 |
| Ala | Pro | Pro | Gly | Gly | Thr | Glu | Arg | Arg | Pro | Asn | Gly | Leu | Gly | Pro | Glu |
|     |     |     |     | 245 |     |     |     |     | 250 |     |     |     |     | 255 |     |
| Arg | Ser | Ala | Gly | Pro | Gly | Gly | Ala | Glu | Ala | Glu | Pro | Leu | Pro | Thr | Gln |
|     |     |     | 260 |     |     |     |     | 265 |     |     |     |     | 270 |     |     |
| Leu | Asn | Gly | Ala | Pro | Gly | Glu | Pro | Ala | Pro | Ala | Gly | Pro | Arg | Asp | Thr |
|     |     | 275 |     |     |     |     | 280 |     |     |     | 285 |     |     |     |     |
| Asp | Ala | Leu | Asp | Leu | Glu | Glu | Ser | Ser | Ser | Ser | Asp | His | Ala | Glu | Arg |
|     | 290 |     |     |     |     | 295 |     |     |     |     | 300 |     |     |     |     |
| Pro | Pro | Gly | Pro | Arg | Arg | Pro | Glu | Arg | Gly | Pro | Arg | Gly | Lys | Gly | Lys |
| 305 |     |     |     |     | 310 |     |     |     |     | 315 |     |     |     |     | 320 |
| Ala | Arg | Ala | Ser | Gln | Val | Lys | Pro | Gly | Asp | Ser | Leu | Arg | Gly | Ala | Gly |
|     |     |     |     | 325 |     |     |     |     | 330 |     |     |     |     | 335 |     |
| Arg | Gly | Arg | Arg | Gly | Ser | Gly | Arg | Arg | Leu | Gln | Gly | Arg | Gly | Arg | Ser |
|     |     |     | 340 |     |     |     |     | 345 |     |     |     |     | 350 |     |     |
| Ala | Ser | Gly | Leu | Pro | Arg | Arg | Arg | Ala | Gly | Ala | Gly | Gly | Gln | Asn | Arg |
|     |     | 355 |     |     |     |     | 360 |     |     |     | 365 |     |     |     |     |
| Glu | Lys | Arg | Phe | Thr | Phe | Val | Leu | Ala | Val | Val | Ile | Gly | Val | Phe | Val |
|     | 370 |     |     |     |     | 375 |     |     |     |     | 380 |     |     |     |     |
| Val | Cys | Trp | Phe | Pro | Phe | Phe | Phe | Thr | Tyr | Thr | Leu | Thr | Ala | Val | Gly |
| 385 |     |     |     |     | 390 |     |     |     |     | 395 |     |     |     |     | 400 |
| Cys | Ser | Val | Pro | Arg | Thr | Leu | Phe | Lys | Phe | Phe | Phe | Trp | Phe | Gly | Tyr |
|     |     |     |     | 405 |     |     |     |     | 410 |     |     |     |     | 415 |     |
| Cys | Asn | Ser | Ser | Leu | Asn | Pro | Val | Ile | Tyr | Thr | Ile | Phe | Asn | His | Asp |
|     |     |     | 420 |     |     |     |     | 425 |     |     |     |     | 430 |     |     |
| Phe | Arg | Arg | Ala | Phe | Lys | Lys | Ile | Leu | Cys | Arg | Gly | Asp | Arg | Lys | Arg |
|     |     | 435 |     |     |     |     | 440 |     |     |     | 445 |     |     |     |     |
| Ile | Val |     |     |     |     |     |     |     |     |     |     |     |     |     |     |
|     | 450 |     |     |     |     |     |     |     |     |     |     |     |     |     |     |

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GTCGACCCTG TGYGYSATCA SCATKGAYMG STA 33

(2) INFORMATION FOR SEQ ID NO:10:

(i) SEQUENCE CHARACTERISTICS:

(A) LENGTH: 35 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

AAGCTTAWGA AGAAGGGSAR CCAGCAGAKS RYGAA 35

(2) INFORMATION FOR SEQ ID NO:11:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GCCATCCAAG GGCCATGTAG GTTTTGCCTT GTGCCAGCTT AGCTGCAC 48

(2) INFORMATION FOR SEQ ID NO:12:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

GACAGGGTTT CCATTACCTG TGGTGGTCTG GCAGTTCTTG GCATGGAC 48

(2) INFORMATION FOR SEQ ID NO:13:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO ( v ) FRAGMENT TYPE:

( v i ) ORIGINAL SOURCE:

( x i ) SEQUENCE DESCRIPTION: SEQ ID NO:13:

TGCCTTCGGA GTCATCTTCC TCTCATACTG GAAAGGGCAG GAGATAGC  48

CDNA ENCODING A RAT $D_1$ DOPAMINE RECEPTOR LINKED TO ADENYLYL CYCLASE ACTIVATION AND EXPRESSION OF THE RECEPTOR PROTEIN IN PLASMID-TRANSFECTED CELL LINES

This application is a continuation of U.S. patent application Ser. No. 08/029,917, filed Mar. 11, 1993, now abandoned, which was a continuation of U.S. patent application Ser. No. 07/548,714, filed Jul. 6, 1990, now abandoned, by the same inventors.

BACKGROUND OF THE INVENTION

1. Technical Field

The present invention relates, in general, to the molecular cloning and expression of a receptor protein, and, in particular, to the $D_1$ dopamine receptor linked to the activation of adenylyl cyclase activity. The invention further relates to a cDNA sequence encoding the $D_1$ dopamine receptor, to a recombinant DNA molecule that includes such a sequence and to cells transformed therewith.

2. Background Information

Dopamine receptors belong to a large class of neurotransmitter and hormone receptors which are linked to their signal transduction pathways via guanine nucleotide binding regulatory (G) proteins, and are amongst the most intensively studied neurotransmitter receptor systems in the brain. Pharmacological, biochemical and physiological criteria have been used to describe two subcategories of dopamine receptors, referred to as $D_1$ and $D_2$. Creese, *Receptor Bio. Chem. and Methodology* 8:1–245 (1987). $D_1$ receptors have been classically defined as being linked to the stimulation of adenylyl cyclase activity and are coupled with the $G_s$ regulatory protein. Krebabian, *Nature* 277:93–96 (1979); Krebabian, *Trends Pharmacol* 7:96–99 (1986). In contrast, activation of $D_2$ receptors results in various responses, including inhibition of adenylyl cyclase activity, inhibition of phosphatidylinositol turnover, increase in K+ channel activity and inhibition of Ca2+ mobilization. Creese, *Ann, Rev. Neurosci* 6:43–71 (1983); Vallar, *Trends Pharmacol* 10:74–77 (1989); Lacey, *J. Physiol.* 392:397–416 (1987); Bigornia, *J. Neurochem.* 51:999–1006 (1988).

The molecular characterization of $D_2$ dopamine receptors has been facilitated by the cloning of a cDNA encoding a rat $D_2$ receptor. Bunzow, *Nature* 336:783–787 (1988). More recently, this receptor has been shown to exist as two protein isoforms which are derived from a single gene yet produced by alternative RNA splicing. Monsma, *Nature* 342:926–929 (1989); Giros, *Nature* 342:923–926 (1989); Selbie, *DNA* 8:683–689 (1989); Dal Toso, *EMBO J.* 8:4025–4034 (1989); Grandy, *Proc. Natl. Acad. Sci.* 86:9762–9766 (1989); Chio, *Nature* 343:266–269 (1990); O'Malley, *Biochemistry* 29:1367–1371. This splice variation occurs in a region of the receptor which may be involved in G protein coupling, suggesting that these receptor isoforms may activate different signal transduction pathways.

Evidence has also accumulated suggesting heterogeneity in the $D_1$ category of dopamine receptors. $D_1$ receptors in renal tissue have recently been described as stimulating phospholipase C activity independently from that of adenylyl cyclase. Felder, *J. Pharm. Exp. Therap.* 248:171–175 (1989); Felder, *J. Biol. Chem.* 264:8739–8745 (1989); Felder, *Am. J. Physiol.* 275:F315–F327 (1989). There has also been shown, using *Xenopus oocyte* expression experiments, that rat striatal mRNA encodes $D_1$ receptors which are coupled to phospholipase C and Ca2+ mobilization in a cAMP-independent fashion. Mahan, *Proc. Natl. Acad. Sci.* 87:2196–2200 (1990). These data suggest that there may be multiple $D_1$ receptors which are coupled to different signal transduction pathways or that a single, multifunctional $D_1$ receptor exists.

Dopamine receptors are extremely important from a clinical therapeutic viewpoint as drugs which activate (agonists) these receptors are used to treat Parkinson's disease and related extrapyramidal disorders as well as hyperprolactinemia, whereas drugs which block (antagonists) dopamine receptors are used to treat schizophrenia and other mental disorders. Despite their clinical utility, one problem with the dopamine agonist and antagonist drugs currently available is that they have many side effects, like many other drugs which work through interacting with receptors. These side effects are predominantly due to a lack of receptor specificity. That is, the drug in use interacts not only with dopamine receptors but with other neurotransmitter receptors as well.

A major goal of clinical neuropharmacology and the pharmaceutical industry is the development of more highly selective drugs with even greater efficacy than those currently in use. Impediments to this process are the low abundance of dopamine receptor protein available to study in neural tissue and the lack of suitable homogeneous model systems of the receptors with which to screen drugs against.

A novel approach to the solution of this problem is to clone cDNAs encoding dopamine receptors, construct eukaryotic expression vectors containing these cDNAs and create a series of stably transfected mammalian cell lines which express functional dopamine receptors in high abundance. These cell lines, which would express a homogeneous population of dopamine receptors, can be used by the pharmaceutical industry or others to screen drugs and study the dopamine receptors using a variety of biochemical, physiological and pharmacological techniques. To accomplish this goal, we have isolated a cDNA encoding the rat $D_1$ dopamine receptor subtype linked to the activation of adenylyl cyclase activity. This cDNA encoding the $D_1$ receptor will be inserted into different eukaryotic expression vectors and used in the construction of various mammalian cell lines expressing this functional protein. The resulting $D_1$ receptor-expressing cell lines can be used to investigate the affinities and efficacies of agonist and antagonist drugs with the $D_1$ receptor using various techniques, such as radioligand binding and second messenger assays.

SUMMARY OF THE INVENTION

It is a object of the present invention to provide a $D_1$ dopamine receptor that is linked to the activation of adenylyl cyclase activity.

It is a further object of our invention to provide a cDNA encoding for the $D_1$ dopamine receptor.

It is another object of the present invention to provide a method of expressing the $D_1$ dopamine receptor cDNA in mammalian cells.

Further objects and advantages of the present invention will be clear from the description that follows.

In one embodiment, the present invention relates to a $D_1$ dopamine receptor that couples with guanine nucleotide binding regulatory (G) proteins and is linked to the stimulation of adenylyl cyclase activity.

In another embodiment, the present invention relates to a DNA fragment encoding the above-described $D_1$ dopamine receptor.

In a further embodiment, the present invention relates to a recombinant DNA construct comprising a vector, and the above-described DNA fragment.

In yet another embodiment, the present invention relates to a host cell transformed with the above-described recombinant DNA construct.

In another embodiment, the present invention relates to a process of producing the above-described $D_1$ dopamine receptor. The method comprises culturing the above-described host cell under conditions such that the above-described DNA fragment is expressed and the $D_1$ dopamine receptor is produced.

FIG. 1: Expression of the $D_1$ receptor cDNA in COS-7 cells assayed by [$^3$H]SCH-23390 binding.

- (A): Saturation isotherms of the total (o), nonspecific (Δ), and specific (o) binding of [$^3$H]SCH-23390 to transfected COS-7 cell membranes. The inset shows a Scatchard transformation of the specific binding data. In this experiment, which was representative of three, the calculated $K_D$ and $B_{MAX}$ values were 0.3 nM and 400 fmol/mg protein, respectively.
- (B): Competition analysis of various dopaminergic ligands for [$^3$H]SCH-23390 binding in COS-7 cell membranes. In this experiment, [$^3$H]SCH-23390 (0.5 nM) was incubated with increasing concentrations of the following ligands: (+)-SCH-23390 (o), (+)-butaclamol (Δ), (−)SCH-23390 (o), spiperone (□), dopamine+GppNHp (■), and (−)-butaclamol (Δ). Average $K_I$ and SEM values from 3 experiments are given in the text.

FIG. 2: $D_1$ receptor stimulation of cAMP production in transfected COS-7 cells.

COS-7 cells were transfected with pSRα-D1 and assayed for cAMP accumulation. Each agonist was tested at a 1 uM concentration in the presence of 0.5 uM of the β-adrenergic antagonist propranolol. Data are presented as amount of cAMP produced over the basal level which corresponded to 17.7 pmol/mg protein. The experiment shown is representative of two different transfection experiments.

DETAILED DESCRIPTION OF THE INVENTION

Figure 1A:
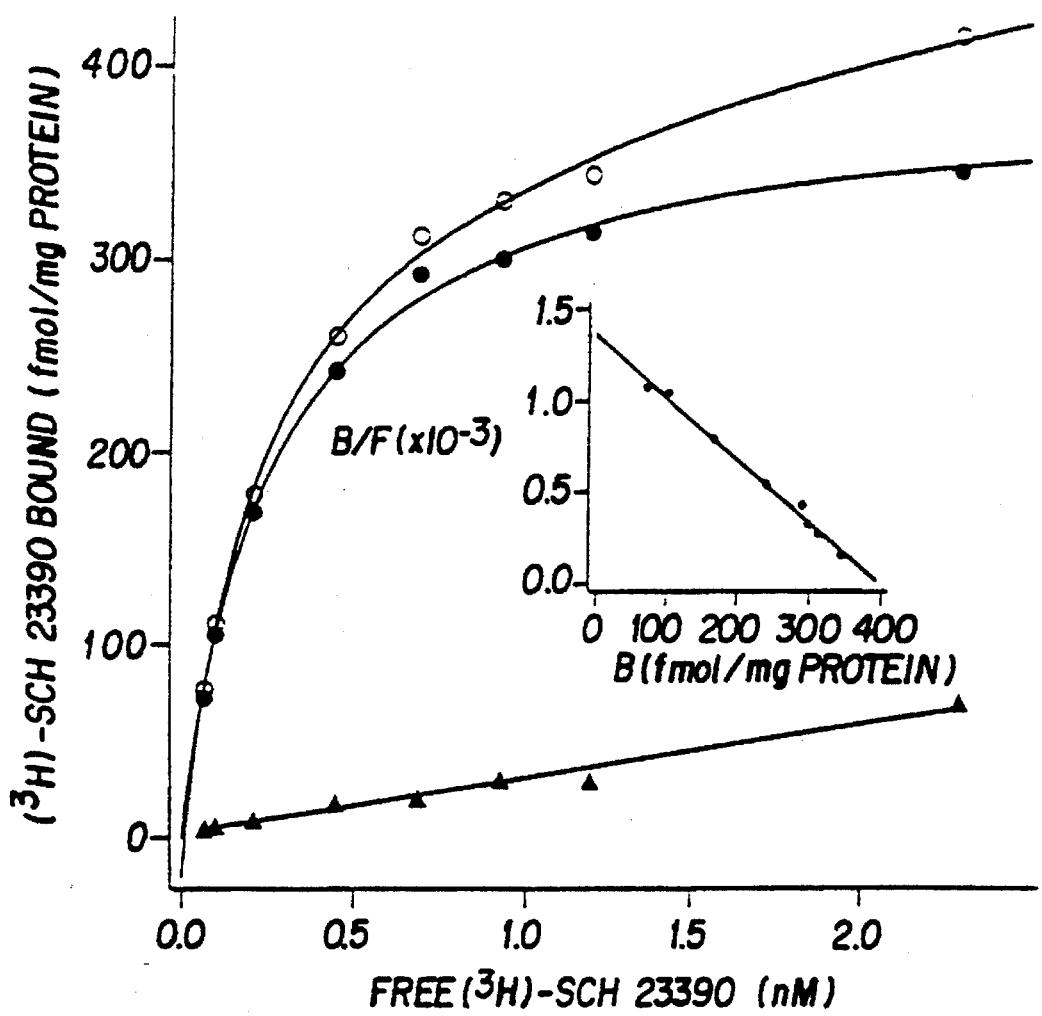

The present invention relates to a $D_1$ dopamine receptor that is linked to the activation of adenylyl cyclase activity and is coupled with the guanine nucleotide binding regulatory ($G_S$) protein. The invention further relates to DNA sequences (fragments) encoding all, or at least 8 amino acids, of the receptor protein. The invention also relates to recombinant construct containing such DNA sequences, and to cells transformed therewith. In a further embodiment, the present invention relates to methods of expressing the receptor gene.

The protein of the present invention is one of a large class of neurotransmitter and hormone receptors which are linked to their signal transduction via guanine nucleotide binding regulatory proteins. Specifically, the $D_1$ receptor is linked to the stimulation of adenylyl cyclase activity, coupling with the $G_S$ regulatory protein. The receptor can have the complete sequence shown in SEQ ID NO:2, and can also have the amino acid sequence of a molecule having substantially the same adenylyl cyclase activation properties, pharmacological properties, and $G_S$ regulatory protein coupling properties of the protein shown in SEQ ID NO:2 (for example, allelic variations of the $D_1$ receptor protein). Alternatively, the receptor protein (or polypeptide) of the invention can have an amino acid sequence corresponding to any portion that is at least 8 amino acids of the protein shown in SEQ ID NO:2 (or allelic variations thereof). As an example, the protein (or polypeptide) can have an amino acid sequence corresponding to an epitope of the sequence shown in SEQ ID NO:2 (or allelic variation thereof).

The receptor can be present in a substantially pure form, that is, in a form substantially free of proteins and nucleic acids with which it is normally associated. The $D_1$ receptor protein can be purified using protocols known in the art. The protein can be used as an antigen, in protocols known in the art, to produce antibodies thereto, both monoclonal and polyclonal.

In another embodiment, the present invention relates, as indicated above, to DNA sequences (including cDNA sequences) that encode the entire amino acid sequence shown in SEQ ID NO:2 (the specific DNA sequence shown in SEQ ID NO:1 being only one example), or any portion comprising at least 24 base pairs thereof. DNA sequences to which the invention relates also include those encoding proteins (or polypeptides) having substantially the same adenylyl cyclase activating properties, pharmacological properties, and $G_S$ regulatory protein coupling properties of the $D_1$ receptor (for example, allelic forms of the amino acid sequence shown in SEQ ID NO:1).

In another embodiment, the present invention relates to a recombinant DNA construct that includes a vector and a DNA sequence as described above (advantageously, a DNA sequence encoding the receptor shown in SEQ ID NO:2 or a receptor having the adenylyl cyclase activating properties, pharmacological properties, and $G_S$ regulatory protein coupling properties of that protein). The vector can take the form of a virus or a plasmid expression vector (for example, λ ZAP II). The DNA sequence can be present in the vector operably linked to regulatory elements, including, for example, a promoter. The recombinant construct can be suitable for transforming procaryotic or eukaryotic cells, advantageously, mammalian cells. For instance, pBluescript plasmids are suitable for transforming bacterial cells, and the pCD-SRα vector is suitable for eukaryotic transformation.

In a further embodiment, the present invention relates to a host cell transformed with the above-described recombinant construct. The host can be procaryotic (for example, bacterial), lower eukaryotic (i.e., fungal, including yeast) or higher eukaryotic (i.e., all mammalian, including but not limited to rat and human). For instance, stable transformations can be accomplished into chinese hamster ovary cells (CHO) or COS-7 cells. Transformation can be effected using methods known in the art. The transformed host cells can be used as a source for the DNA sequence described above (which sequence constitutes part of the recombinant construct). When the recombinant receptor takes the form of an expression system, the transformed cells can be used as a source for the above-described receptor.

The presence of the $D_1$ receptor protein can be detected in a sample (for instance, tissue from a human or other mammal, or a cell culture) by contacting the sample with an antibody to the receptor. The detection of the presence or absence of a complex formed between the receptor and the antibody may be accomplished by methods well known in the art. The presence of a DNA segment encoding the $D_1$ receptor protein can be detected in a sample (for instance, tissue from a human or other mammal, or a cell culture) by contacting the sample with a DNA probe that is comprised of the DNA segment. Using methods well known in the art and under conditions such that hybridization will occur, a complex can be formed between the probe and the DNA segment from the sample. Detection of the presence or absence of the complex may be accomplished by methods well known in the art.

The $D_1$ dopamine receptor protein and nucleic acid sequences of the present invention can be used both in a research setting (for example, to facilitate an understanding of receptor protein mechanisms) and in a clinical setting (for example, to use an a model system of the receptor with which to screen agonist and antagonist drugs against). For instance, therapeutic drugs designed to interact with dopamine receptors often have side effects. A cell line expressing the $D_1$ receptor can be used to investigate the affinities and efficacies of agonist and antagonist drugs, with the $D_1$ receptor using various techniques, such as radioligand binding and second messenger assays. The activity of the drug-treated cell can be compared to a control cell to evaluate the activation or blocking of the $D_1$ receptor.

For diagnostic purposes, expression of the $D_1$ receptor cDNA in cells can be measured using known methods. To accomplish this, antibodies to the $D_1$ receptor (prepared by producing all or portions of the $D_1$ receptor protein and injecting these into various types of animals, e.g, rabbits, sheep, goats or mice) can be used.

The invention is described in further detail in the following non-limiting Examples.

EXAMPLES

The following technical protocols are used in the examples that follow:

Polymerase chain reaction. Poly(A)+ RNA was prepared from NS20Y cells exactly as described in Mahan, *Proc. Natl. Acad. Sci.*, 87:2196–2200 (1990). First strand cDNA synthesis was performed using this RNA template in the presence of AMV-reverse transcriptase (Promega) and 1 ug of oligo dT primer. This cDNA was subsequently submitted to 30 cycles of polymerase chain reaction (PCR) amplification in a total reaction volume of 100 ul with 1 uM each of the following primers:

5'-GTCGACCCTGTGC(T)GC(T)C(G)ATCAG(C)CATG(T)GAT(C)C(A)GC(G)TA-3' (SEQ ID NO:9)

and

3'AAGT(C)G(A)G(C)G(T)AGACGACCG(A)AC(G)GGGAAGAAGT(A)ATTCGAA-5' (SEQ ID NO:10)

and Taq DNA polymerase (Perkin Elmer-Cetus). The timing used was 1.5 minutes at 93 degrees celsius, 2 minutes at 55 degrees celsius, and 4 minutes at 72 degrees celsius, followed by a 7 minute extension at 72 degrees celsius. The reaction products were purified by electrophoresis in 1% LMP agarose (Bethesda Research Labs.). Individual bands were excised from the gel, phenol extracted, ethanol precipitated, digested with Sal I and Hind III and ligated into Sal I/Hind III digested pGEM 9Zf(–) (Promega). Competent XL1-Blue cells (Stratagene) were transformed and mini-preparations of plasmid DNA prepared for insert sequencing as described below.

cDNA library screening and DNA sequencing. $1 \times 10^6$ recombinants from a rat striatal cDNA library, constructed in the λ ZAP II vector (Stratagene), were screened with a PCR fragment which was $P^{32}$-labelled via nick translation. Duplicate nitrocellulose filters were hybridized in 50% formamide, 0.75M NaCl/0.075M sodium citrate (5×SSC), 5×Denhardt's solution, 0.02M $Na_2HPO_4$, 0.25% SDS, 0.15 mg/ml salmon sperm DNA, and $4 \times 10^6$ dpm/ml of $P^{32}$-labelled probe for 24 hours at 37 degrees celsius. High stringency washing of the filters was performed with 1×SSC and 0.1% SDS at 65 degrees celsius prior to autoradiography. λ phage found to hybridize to the probe were subsequently plaque purified. In vivo excision and rescue of the nested pBluescript plasmids from the λ ZAP II clones were performed using helper phage according to the Stratagene protocol. Nucleotide sequence analysis was performed using the Sanger dideoxy nucleotide chain termination method with Sequenase (US Biochemical Corp.) both on denatured double-stranded plasmid templates and on single-stranded templates as described in Brumbaugh, *Proc. Natl. Acad. Sci.*, 85:5610–5614 (1988). Primers were synthetic oligonucliotides which were either vector-specific or derived from prior sequence information. In some cases a series of nested deletion mutants were constructed using the Exo III/S1 nuclease procedure (Promega) prior to DNA sequencing.

mRNA analysis. Northern blot and in situ hybridization histochemical analyses were performed exactly as previously described in Monsma, *Nature*, 342:926–929 (1989), using the following oligonucleotide probes:

5'-GCCATCCAAGGGCCATGTAGGTTTTGC-CTTGTGCCAGCTTAGCTGCAC-3' (SEQ ID NO:11)    (1)

5'-GACAGGGTTTCCATTACCTGTGGTG-GTCTGGCAGTTCTTGGCATGGAC-3' (SEQ ID NO:12)    (2)

and

5'-TGCCTTCGGAGTCATCTTCCTCTCAT-ACTGGAAAGGGCAGGAGATAGC-3' (SEQ ID NO:13)    (3)

These were radiolabelled using terminal deoxytransferase with either [α-$^{32}$P]ATP (Northern blots) or [α-$^{35}$S]ATP (in situ hybridization).

Expression studies, A full-length cDNA insert, including the multiple cloning site of the λ ZAP II vector, was amplified from the purified λ phage clone using T3 and T7 promoter primers and PCR as described above. The reaction product was phenol extracted, ethanol precipitated, sequentially digested with Not I and Kpn I and ligated into Not I/Kpn I digested pCD-SRα (Takebe, *J. Molec. Cell. Biol.* 8:466–472 (1988)) containing a modified polylinker. Competent DH5α cells were transformed and clones containing the appropriate cDNA insert were used for large-scale plasmid preparations via the CsCl gradient purification method. DNA from the resulting plasmids was used to transiently transfect COS-7 cells by the $CaPO_4$ precipitation technique (Chen, *J. Molec. Cell. Biol.* 7:2745–2752 (1987)). The cells were treated with 3 mM sodium butyrate after 48 hours and were harvested after 72 hours. Membranes were prepared and assayed for $D_1$ receptor binding activity using [$^3$H]SCH-23390 (Dupont/NEN) exactly as described in Mahan, *Proc. Natl. Acad. Sci.*, 87:2196–2200 (1990). Intact cells were also used for cAMP assays which were performed as described previously in Monsma, *Brain Research*, 492:314–324 (1990). Protein concentrations were determined using the bicinchoninic acid (BCA) protein reagent (Pierce) as described in Smith, *Anal. Biochem.*, 150:76–85 (1985).

EXAMPLE I

Isolation and Characterization of cDNA Clones for a $D_1$ receptor (i) Cloning and sequencing analyses of $D_1$ receptor cDNA:
In order to clone the $D_1$ dopamine receptor linked to adenylyl cyclase activation, the PCR method was used to selectively amplify cDNA sequences from mRNA purified from mouse NS2OY neuroblastoma cells, which has previously been shown to express this receptor subtype. Monsma, *Brain Research*, 492:314–324 (1989). Poly(A)+ RNA was used to first synthesize cDNA by reverse transcription followed by PCR amplification with a pair of highly degenerate primers derived from the third and sixth transmembrane regions of the previously cloned adrenergic, $D_2$ dopaminergic, and serotonin receptors. This process resulted in the amplification of several cDNA fragments.

These fragments were preliminarily characterized by DNA sequence analysis. One of these fragments was found to exhibit considerable sequence homology to previously cloned G protein-coupled receptors and was subsequently used to screen a rat striatal cDNA library in order to isolate a full-length clone. Four cDNA clones with insert sizes ranging from about 2.8 to 3.8 kb were isolated, all of which strongly hybridized with the $P^{32}$-labelled PCR probe on dot-blot analysis. One of these clones (pB73D1) with an insert of about 3.6 kb was sequenced and found to exhibit more than 90% nucleotide sequence homology in the region of the PCR fragment, the divergence of which is probably attributable to species differences (mouse vs. rat). The *E. coli* strain XL-1 Blue containing plasmid pB73D1 is maintained as a Budapest Treaty Patent Deposit by the American Type Culture Collection, 12301 Parklawn Drive, Rockville, Md. 28052, under Accession Number 68356, made Jun. 29, 1990.

The nucleotide and deduced amino acid sequence for clone pB73D1 is shown in SEQ ID NOS:1 and 2, respectively. The longest open reading frame in this cDNA codes for a 487 residue protein with a theoretical molecular weight of 54,264 Da. Although the neighboring sequence of the first ATG in this reading frame is similar to Kozak's consensus initiation sequence (Kozak, *Nucleic Acids Res.*, 12:857–872 (1984), the third Met codon at position 49 actually provides a better match. The longest reading frame is preceded 292 nucleotides which contains a small open reading frame from nucleotides −259 to −154.

Hydrophobicity analysis of the translated protein of the translated protein reveals seven clusters of about 24 hydrophobic residues, predicted to represent transmembrane-spanning domains, connected by three extracellular and three intracellular loops. This pattern is similar to that observed for other cloned G protein-coupled receptors where the $NH_2$ terminus is proposed to be extracellular and the COOH terminus projects into the cytoplasm. Dohlman, *Biochemistry*, 26:2657–2664 (1987). The $NH_2$ terminus contains one consensus site for N-linked glycosylation (Asn 45) while the predicted third cytoplasmic loop exhibits one consensus recognition site for phosphorylation by the cAMP-dependent protein kinase Ser (270). In addition, the long COOH terminus contains several serine and threonine residues possibly representing additional sites for regulatory phosphorylation. Sibley, *Cell*, 48:913–922 (1987).

(ii) Characterization of the amino acid sequence for the pB73D1 clone. Comparison of the deduced amino acid sequence for the pB73D1 cDNA clone with the sequences of various catecholamine receptors indicates that the regions of highest identity appear to occur within the predicted transmembrane spanning domains. Within these regions, the pB73D1 protein exhibits sequence homologies of 44% with the rat $D_2$ dopaminergic receptor SEQ ID NO:3; 44%, 43% and 40% with the human β-1-, β-2-, and β-3-adrenergic receptors (SEQ ID NOS:4–6) respectively; and 43% and 42% with the hamster α1B- and human α2A-adrenergic receptors (SEQ ID NOS:7–8), respectively. The $NH_2$ and COOH termini and the extracellular and intracellular loops are significantly more divergent among these receptors. It is interesting to note that within the third putative transmembrane spanning domain of pB73D1, there is conserved aspartate residue which is common to all biogenic amine receptors that have been sequenced thus far. Strader, *FASEB J.*, 3:1825–1832 (1989). Moreover, the fifth transmembrane spanning domain of pB73D1 also contains two serine residues which are conserved among catecholamine receptors and are critical for the recognition of agonist ligands possessing a catechol group. Strader, *FASEB J.*, 3:1825–1832 (1989). These observations suggest the pB73D1 clone encodes a receptor for an endogenous catecholamine ligand.

EXAMPLE II

Establishing the Identity of pB73D1

In an initial attempt to establish the identity of pB73D1, the tissue distribution of its corresponding mRNA was analyzed by Northern blot and in situ hybridization analyses.

(i) Northern blot analysis. Northern blot analysis, in various neural tissues reveals a transcript size of about 4 kb which is predominantly located in the striatum with lesser amounts in the cortex and retina. In contrast, no mRNA is observed in the cerebellum, hippocampus, olfactory bulb, mesencephalon, or pituitary. These data also indicate that the 3.6 kb pB73D1 clone is nearly full length.

(ii) In situ hybridization. In situ hybridization analysis also indicates a high abundance of mRNA in the striatum, including the caudate-putamen and nucleus accumbens, as well as in the olfactory tubercle. Approximately half of the medium sized neurons in the striatum are identified using this technique, which is typical of the striatum as a whole. The tissue distribution of pB73D1 mRNA is remarkably similar to that of the $D_1$ dopamine receptor as demonstrated by receptor binding and autoradiography studies. Creese, *Receptor Biochemistry and Methodology: Dopamine Receptors*, 8:1–245 (1987).

EXAMPLE III

Establishing the Identity of the Receptor Encoded by the pB73D1 clone

To definitively establish the identity of the receptor encoded by the pB73D1 clone, the cDNA insert was subcloned into the pCD-SRα vector (Takebe, *J. Molec. Cell. Biol.*, 8:466–472 (1988)) for expression in eukaryotic cells. The resulting plasmid, pSR2α-D1, was used to transiently transfect COS-7 cells.

(i) Expression of the $D_1$ receptor cDNA in COS-7 cells assays.

Expression of the $D_1$ receptor cDNA in COS-7 cells assayed by a $D_1$-selective radiolabelled antagonist ([$^3$H]SCH-23390), as shown in FIG. 1A, demonstrates that an antagonist binds to COS-7 membranes in a saturable fashion with high specific activity (about 400 fmol/mg protein) and an affinity (0.3+/−0.03 nM) in good agreement with that found in the rat striatum. Creese, *Receptor Biochemistry and Methodology: Dopamine Receptors*, 8:1–245 (1987). No specific binding was detected in COS-7 cells that had not been transfected with pSRα-D1 or transfected with the pCD-SRα vector alone.

Figure 1B:
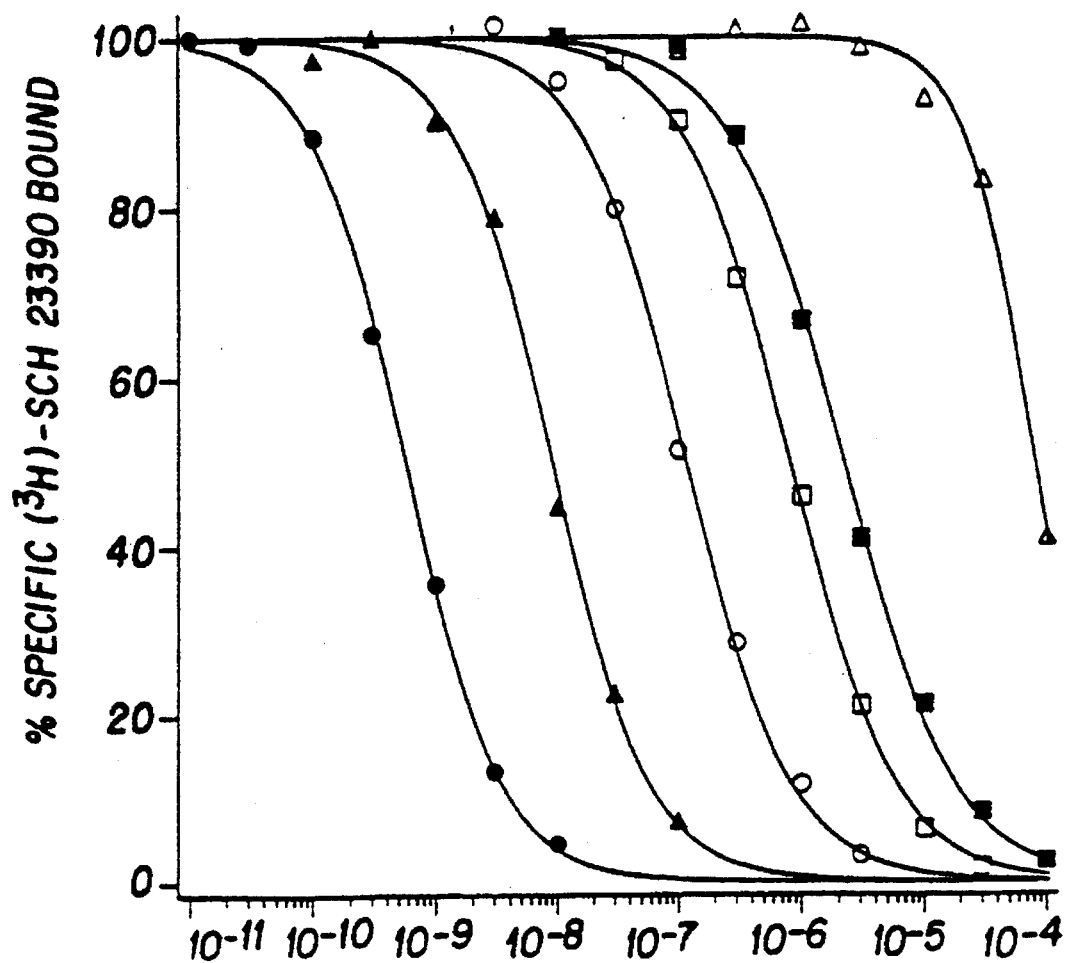

(ii) Competition analysis of various dopaminergic ligands. FIG. 1B demonstrates the ability of a variety of dopaminergic ligands to compete for specific [$^3$H]SCH-23390 binding to transfected COS-7 cell membranes. (+)-SCH-23390 is the most potent agent (0.2+/–0.02 nM) and is approximately 200-fold more potent than its enantiomer, (–)-SCH-23388 (41+/–1.2 nM). The non-selective dopaminergic antagonist (+)-butaclamol also exhibits high affinity (2.8+/–0.2 nM) and is more than 4 orders of magnitude more potent than its inactive isomer, (–)-butaclamol (31+/–0.8 uM). The $D_2$-selective antagonist spiperone exhibits relatively low affinity (290+/–7 nM) as do the serotonin antagonists, ketanserin (0.42+/–0.031 uM) and mianserin (0.18+/–0.042 uM). The endogenous agonist, dopamine, is also able to completely inhibit [$^3$H]SCH-23390 binding (0.64+/–0.092 uM). This rank order of potency as well as the absolute affinities ($K_i$) of these compounds agree well with those previously demonstrated for striatal $D_1$ receptors. Creese, *Receptor Biochemistry and Methodology: Dopamine Receptors*, 8:1–245 (1987).

Figure 2:
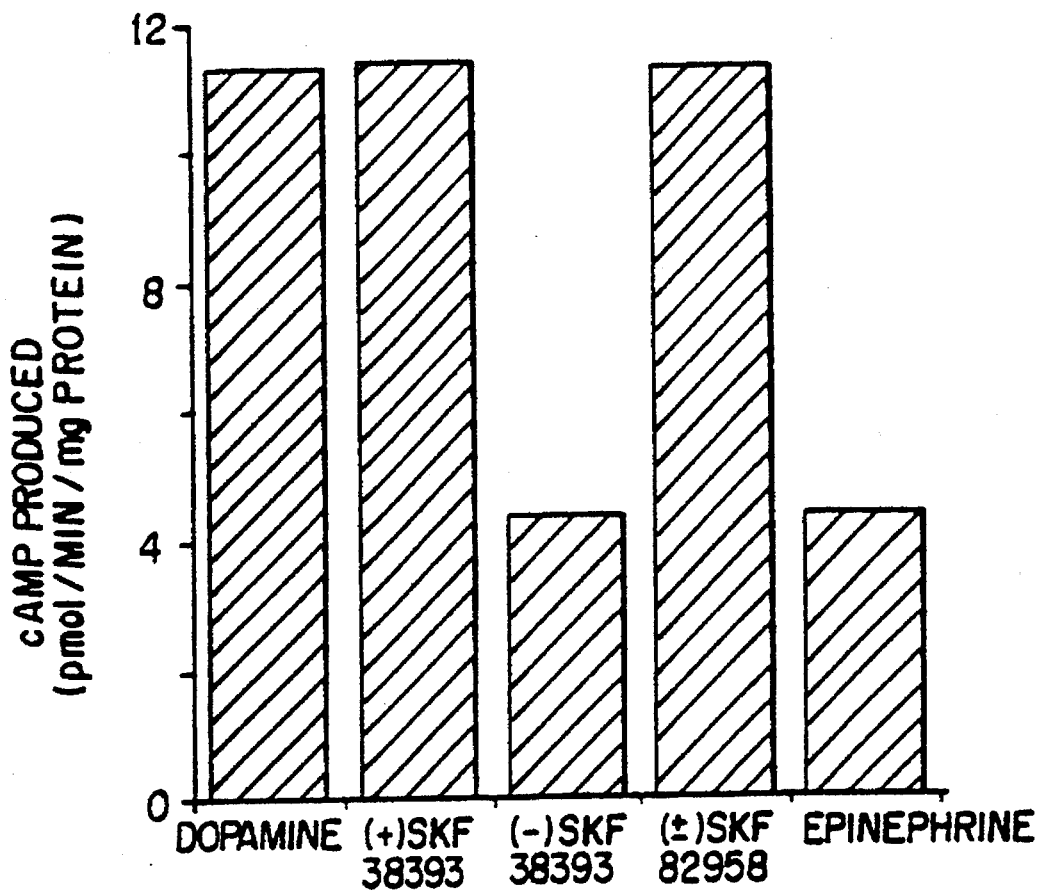

(iii) Receptor-mediated stimulation of cAMP production. FIG. 2 demonstrates that pSRα-D1-transfected COS-7 cells also exhibit $D_1$ receptor-mediated stimulation of cAMP production. Dopamine stimulates cAMP production by approximately 2-fold in these transfected cells. FIG. 2. In contrast, no response to dopamine is observed in non-transfected COS-7 cells. The $D_1$ selective agonists (+)SKF-38393 and (+/–)SKF-82958 also stimulate cAMP accumulation to a similar extent as dopamine. In addition, the stimulation by SKF-38393 exhibits appropriate stereoselectivity with the (–)isomer exhibiting a lower potency. FIG. 5. Finally, the β-adrenergic agonist, epinephrine, also exhibits a low potency relative to dopamine as expected for a $D_1$ receptor. In these experiments, the β-adrenergic antagonist propranolol was included in the assays to preclude stimulation of the endogenous COS-7 cell β-adrenergic receptor.

These expression data confirm that the cDNA which has been cloned encodes a functional $D_1$ dopamine receptor protein that is capable of ligand binding interactions and stimulation of adenylyl cyclase activity. This conclusion is further supported by the observation that mRNA corresponding to this cDNA is localized in tissues where $D_1$ dopamine receptors are known to be selectively expressed. Comparison of the sequence of this newly cloned dopamine receptor with the sequences of other previously cloned catecholamine receptors reveals a number of interesting homologies. As mentioned above, the regions of higher identity between the $D_1$ and other catecholamine receptors occur within the predicted transmembrane spanning domains. Recent mutagenesis studies of the β-adrenergic receptors have indicated that these domains are highly critical for ligand binding activity. Strader, *FASEB J.*, 3:1825–1832 (1989); O'Dowd, *Ann. Rev. Neurosci.*, 12:67–83 (1989). Importantly, the fifth transmembrane domain of the $D_1$ receptor also contains two conserved serine residues (Ser 239 and Ser 240) which are postulated to be involved in the recognition of agonist ligands possessing a catechol group. Strader, *FASEB J.*, 3:1825–1832 (1989). Outside of the transmembrane regions, the areas of homology between the $D_1$ and other catecholamine receptors are less pronounced. It is interesting to note, however, that the size of the cytoplasmic loop between transmembrane segments 5 and 6 is similar to those seen in the β-adrenergic receptors. This loop has recently been implicated in the coupling of β-adrenergic receptors to the $G_S$ regulatory protein and thus the activation adenylyl cyclase. Strader, *FASEB J.*, 3:1825–1832 (1989); O'Dowd, *Ann. Rev. Neurosci.*, 12:67–83 (1989).

(iv) *Xenopus* oocyte expression experiments. It is important to emphasize that the $D_1$ receptor which has been cloned is one which is functionally coupled to the stimulation of adenylyl cyclase. Recently, unique $D_1$ receptors have been described in kidney which stimulate phospholipase C activity independently from the activation of adenylyl cyclase. Felder, *J. Pharm. Exp. Therap.*, 248:171–175 (1989); Felder, *J. Biol. Chem.*, 264:8739–8745 (1989); Felder, *Am. J. Physiol.*, 275:F315–F327 (1989). We have also found, using *Xenopus* oocyte expression experiments, that rat striatum contains mRNA encoding $D_1$ receptors which can couple to phospholipase C, inositol phosphate production and Ca2+ mobilization in a cAMP-independent fashion. Mahan, *Proc. Natl. Acad. Sci. U.S.A.*, 87:2196–2200 (1990). It is interesting that the mRNA which codes for this $D_1$ receptor-stimulated phospholipase C response is about 2.5 kb in size (Mahan, *Proc. Natl. Acad. Sci. U.S.A.*, 87:2196–2200 (1990)) in comparison with the about 4 kb $D_1$ receptor mRNA observed here. Moreover, in preliminary experiments, there has been found that when mRNA is transcribed from the pB73D1 $D_1$ receptor cDNA clone and injected into *Xenopus oocytes*, dopamine will stimulate cAMP accumulation about 2-fold but is incapable of producing a Ca2+ mobilization response. These findings suggest that the striatum contains two separate $D_1$ receptor proteins which are coupled to different signal transduction pathways. Consequently, it is proposed that the $D_1$ receptor subtypes linked to the activation of adenylyl cyclase and phospholipase C be designated $D_{1A}$ and $D_{1B}$.

The entire contents of all references cited herein above incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. An isolated DNA fragment that encodes a $D_1$ dopamine receptor having the amino acid sequence set forth in SEQ ID NO:2.

2. The DNA fragment according to claim 1, wherein said fragment has the sequence of bases designated in SEQ ID NO:1.

3. A DNA fragment according to claim 1, comprising at least 24 bases of the sequence set forth in SEQ ID NO:1 between nucleotide position 293 and nucleotide position 1763, inclusive.

4. A recombinant DNA construct comprising:
   i) a vector, and
   ii) a DNA fragment that encodes the amino acid sequence set forth in SEQ ID NO:2.

5. The recombinant DNA construct according to claim 4, wherein the sequence of said DNA fragment is the DNA sequence set forth in SEQ ID NO:1.

6. The recombinant DNA construct according to claim 4, wherein said vector is a eukaryotic expression vector.

7. The recombinant DNA construct according to claim 4, wherein said DNA fragment comprises at least 24 contiguous bases of the nucleotide sequence set forth in SEQ ID NO:1.

8. A host cell transformed with the recombinant DNA construct according to claim 4.

9. The host cell according to claim 8, wherein said cell is a mammalian cell.

* * * * *